United States Patent
Abdalla

(10) Patent No.: US 11,389,666 B2
(45) Date of Patent: *Jul. 19, 2022

(54) ANCHORED BRACHYTHERAPY DEVICE

(71) Applicant: Positive Energy, LLC, Springfield, MO (US)

(72) Inventor: Ibrahim Abdalla, Springfield, MO (US)

(73) Assignee: POSITIVE ENERGY, LLC, Springfield, MO (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/837,140

(22) Filed: Apr. 1, 2020

(65) Prior Publication Data

US 2020/0222721 A1 Jul. 16, 2020

Related U.S. Application Data

(63) Continuation of application No. 15/873,486, filed on Jan. 17, 2018, now Pat. No. 10,646,727.

(60) Provisional application No. 62/585,303, filed on Nov. 13, 2017.

(51) Int. Cl.
*A61N 5/10* (2006.01)

(52) U.S. Cl.
CPC .......... *A61N 5/1007* (2013.01); *A61N 5/1015* (2013.01); *A61N 2005/1011* (2013.01); *A61N 2005/1024* (2013.01)

(58) Field of Classification Search
CPC ................ A61N 5/1007; A61N 5/1015; A61N 2005/1011
See application file for complete search history.

(56) References Cited

U.S. PATENT DOCUMENTS

| | | |
|---|---|---|
| 4,819,618 A | 4/1989 | Liprie |
| 6,248,057 B1 | 6/2001 | Mavity et al. |
| 6,419,621 B1 | 7/2002 | Sioshansi et al. |
| 6,589,502 B1 | 7/2003 | Coniglione et al. |
| 6,632,176 B2 | 10/2003 | McIntire et al. |
| 6,716,156 B2 | 4/2004 | Menuhr et al. |
| 6,746,661 B2 | 6/2004 | Kaplan |

(Continued)

FOREIGN PATENT DOCUMENTS

WO 0038579 A9 9/2001

OTHER PUBLICATIONS

Elliott, S. L., et al., "Practical considerations in the selection of seed strength for prostate implants", Journal of Applied Clinical Medical Physics, vol. 16, Issue 5, pp. 53-61 (2015).

(Continued)

*Primary Examiner* — John P Lacyk
(74) *Attorney, Agent, or Firm* — Shook, Hardy & Bacon L.L.P.

(57) ABSTRACT

Aspects herein are directed to an anchorable brachytherapy device configured to be permanently implanted in a tumor bed at the time of operative removal of the tumor. In exemplary aspects, the brachytherapy device may comprise a plurality of hollow tubes that form a spherical or ellipsoid shape. Protrusions or grooves may be formed on an outer surface of the tubes to help anchor the brachytherapy device in the tumor bed. Radioactive seeds or strands may be positioned within the tube channels to provide radiation to the tumor bed.

12 Claims, 15 Drawing Sheets

(56) References Cited

U.S. PATENT DOCUMENTS

| | | |
|---|---|---|
| 6,749,553 B2 | 6/2004 | Brauckman et al. |
| 7,083,566 B2 | 8/2006 | Tornes et al. |
| 7,131,942 B2 | 11/2006 | Taylor et al. |
| 7,702,378 B2 | 4/2010 | Bolan et al. |
| 7,862,497 B2 | 1/2011 | Cutrer et al. |
| 7,887,476 B2 | 2/2011 | Hermann et al. |
| 8,137,256 B2 | 3/2012 | Cutrer et al. |
| 8,157,717 B2 | 4/2012 | Cutrer et al. |
| 8,226,539 B2 | 7/2012 | Cutrer et al. |
| 8,257,241 B2 | 9/2012 | Cutrer et al. |
| 8,366,598 B2 | 2/2013 | Lamoureux et al. |
| 8,821,364 B2 | 9/2014 | Fisher et al. |
| 8,827,884 B2 | 9/2014 | Ribbing et al. |
| 9,014,787 B2 | 4/2015 | Stubbs et al. |
| 9,327,061 B2 | 5/2016 | Govil et al. |
| 9,486,642 B2 | 11/2016 | Cipriani et al. |
| 10,646,727 B2 * | 5/2020 | Abdalla ............... A61N 5/1015 |
| 2004/0064011 A1 | 4/2004 | Grabowy et al. |
| 2009/0018383 A1 | 1/2009 | Corcione et al. |
| 2009/0312593 A1 | 12/2009 | Drobnik et al. |
| 2010/0210891 A1 | 8/2010 | Drysen et al. |
| 2013/0289390 A1 | 10/2013 | Hermann et al. |
| 2015/0335783 A1 | 11/2015 | Kohn et al. |
| 2017/0120073 A1 | 5/2017 | Brachman et al. |

OTHER PUBLICATIONS

Yu, Y., et al., "Permanent prostate seed implant brachytherapy: Report of the American Association of Physicists in Medicine Task Group No. 64", Medical Physics, vol. 26, Issue 10, pp. 2054-2076 (Oct. 1999).

Non-Final Office Action dated Sep. 23, 2020, in U.S. Appl. No. 16/373,129, 8 pages.

Notice of Allowance dated Oct. 14, 2020, in U.S. Appl. No. 16/373,129, 5 pages.

* cited by examiner

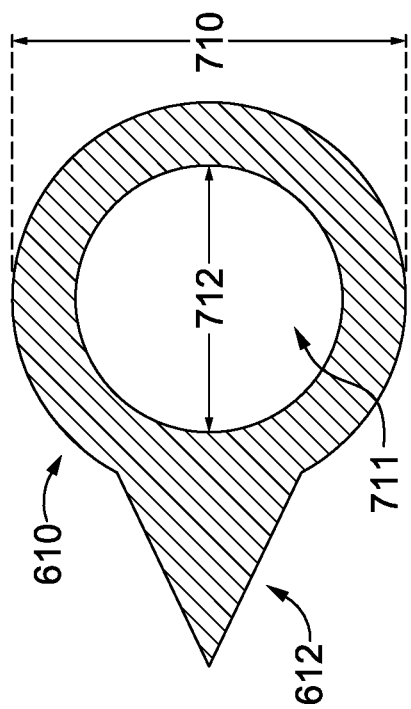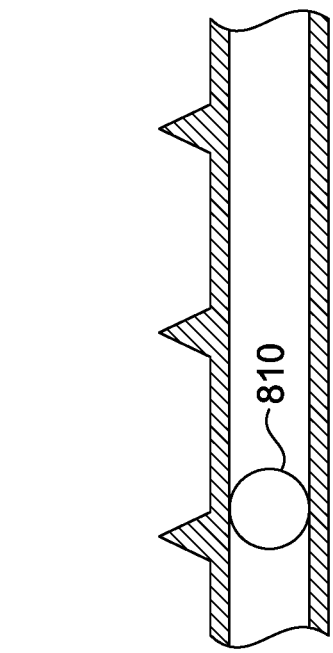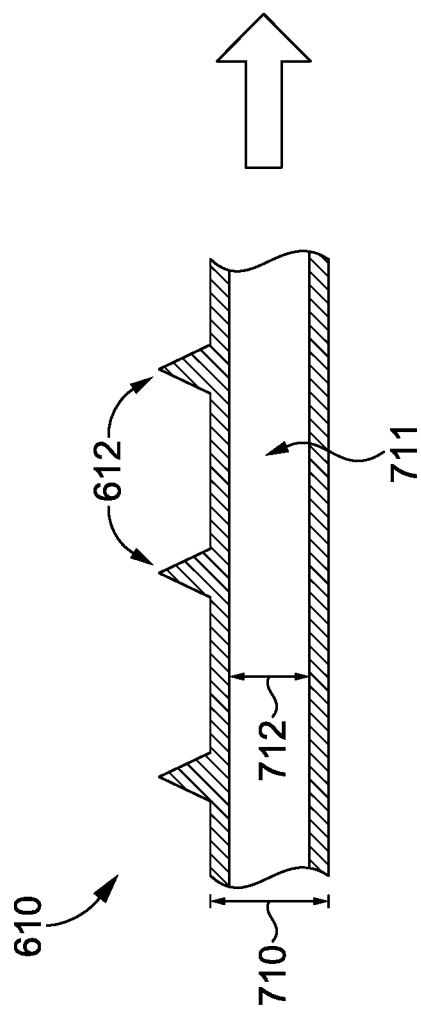

ANCHORED BRACHYTHERAPY DEVICE

CROSS-REFERENCE TO RELATED APPLICATIONS

This application, having Ser. No. 16/837,140 and entitled "Anchored Brachytherapy Device," is a Continuation Application of U.S. application Ser. No. 15/873,486, entitled "Anchored Brachytherapy Device, and filed Jan. 17, 2018, which claims the benefit of priority of U.S. Prov. App. No. 62/585,303, entitled "Anchored Brachytherapy Device," and filed Nov. 13, 2017. The entireties of the aforementioned applications are incorporated by reference herein.

TECHNICAL FIELD

Aspects herein relate to an anchored, permanently implantable brachytherapy device.

BACKGROUND

Radiation therapy, or brachytherapy, is a known modality for treating certain types of tumors such as, for example, breast tumors, brain tumors, lung tumors, sarcomas, and the like and has been shown to result in good tumor control. Brachytherapy may be used by itself or in combination with other therapies such as surgical resection, and/or chemotherapy. Radiation therapy has traditionally been administered using external beam radiation and/or by temporarily delivering a radioactive source to a tumor site via, for example a catheter. Both of these treatment modalities take days to weeks to complete and can be expensive, inconvenient to the patient, time-consuming to the patient and the treatment staff, and potentially painful to the patient. For example, catheter-based partial breast radiation may take five to eight days, and the patient has to be treated twice a day, six hours apart, and the catheter stays in the patient for two to three weeks. During this time, the catheter tail protrudes outside of the patient causing pain and a possible infection risk. Moreover, catheter-based radiation requires planning prior to each treatment which is time-consuming and expensive. Because of this, some patients may opt for more radical, but sometimes unnecessary, treatment options such as, for example, mastectomy instead of lumpectomy and adjuvant radiation with respect to breast cancer.

SUMMARY OF INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Aspects herein are directed to an implantable and anchorable brachytherapy device. Aspects herein may also be directed to an implantable and anchorable stereotactic marker device. With respect to the implantable and anchorable brachytherapy device, aspects herein contemplate a bioabsorbable or biocompatible, three-dimensional (3-D) or two-dimensional (2-D) device that can be, for instance, permanently introduced into a tumor bed at the time of surgical resection of the tumor and which does not need to be removed. As such, the brachytherapy devices described herein provide a convenient and cost-effective alternative to traditional catheter-based and/or external beam radiation options. Moreover, because the device is enclosed within the tumor bed, there are no catheter tails protruding from the patient, which lowers the risk of pain, bleeding, and infection. Further, because the device is anchored within the tumor bed, the risk of device rotation and/or migration is reduced. Additionally, in some instances, filling the void caused by surgical removal of the tumor with one of the devices described herein may be associated with a better cosmetic outcome as described below.

In one exemplary aspect, the device comprises a plurality of grooves, a plurality of projections, and, optionally, one or more central channels extending through the device body. Prior to placement within the tumor bed, one or more low-dose radioactive sources (e.g., seeds or strands) are secured in the grooves. As well, one or more low-dose radioactive sources and/or high-dose radioactive sources may be secured in the central channels. Once placed within the surgical site, the projections help to anchor the device to prevent or minimize shifting, migration, rotation, or movement of the device during radiation delivery. This, in turn, enables a more accurate radiation delivery to the intended area of the patient's body.

In another exemplary aspect, the device comprises one or more hollow tubes having grooves and/or projections. In one configuration, the device comprises a single, continuous hollow tube formed into a helical shape having a vacancy or space at its center. Radioactive seeds or strands may be loaded into the tube channel before intra-operative placement. The grooves and/or projections may be used to anchor the device once placed within the tumor bed. In a second configuration, the device comprises a plurality of hollow tubes formed into, for example, a spherical or ellipsoid shape having a vacancy at its center. Radioactive seeds or strands may be loaded into one or more of the tube channels prior to intra-operative placement. The grooves and/or projections may be used to anchor the device after placement.

Continuing with respect to the hollow tube configurations, because each of these configurations has a vacancy at its center, it can be considered a non-space (or minimally space-) occupying device making it useful in closed-space locations such as, for example, the brain to avoid increases in intracranial pressure. Further, the vacancy at the center of the device may allow for migration or influx of any blood, secretions, or other inflammatory fluids produced by the tumor bed thereby minimizing the opportunity for these fluids to accumulate between the tumor bed and the device wall which may decrease the effectiveness of the radiation treatment.

The brachytherapy devices as contemplated herein provide a customizable, accurate, and sustained delivery of radiation while requiring minimal physician and patient intervention after placement. Further, the brachytherapy devices as contemplated herein may help minimize side effects due to, for instance, infection or radiation damage. As well, in cases such as placement after a breast lumpectomy, the insertion of a 3-D brachytherapy device may provide a pleasing cosmetic effect to the breast.

The 2-D or 3-D device as described herein may also be used as a stereotactic marker device. Stereotactic marker devices typically comprise one more radiopaque markers, and, once positioned within a tumor site, the device may be used to guide, for example, external beam radiation. In one exemplary aspect, the devices described herein may comprise both a brachytherapy device and a stereotactic marker device. With respect to this aspect, both radioactive seeds/ strands and radiopaque markers can be placed in the device grooves, the device central channels, or in the device tube channels. In other exemplary aspects, the devices described herein may be used as just a brachytherapy device or as just a stereotactic marker device. As such, the term "brachytherapy device" as used herein may comprise both a device used to deliver therapeutic radiation and/or a device that is useable as a stereotactic marker.

Additional objects, advantages, and novel features of the invention will be set forth in part in the description which follows, and in part will become apparent to those skilled in the art upon examination of the following, or may be learned by practice of the invention.

BRIEF DESCRIPTION OF THE DRAWINGS

Examples of the present invention are described in detail below with reference to the attached drawing figures, wherein:

FIG. 7 illustrates a cross-section of the hollow tube of the brachytherapy device of, for example, FIG. 6A or 6B where the cross-section is taken along cut line 7-7 of FIG. 6A in accordance with aspects herein;

FIG. 8 illustrates a longitudinal cross-section of the hollow tube of the brachytherapy device of, for example, FIG. 6A or 6B both without and with a radioactive seed and/or radiopaque marker positioned therein in accordance with aspects herein;

DETAILED DESCRIPTION

Figure 1A:
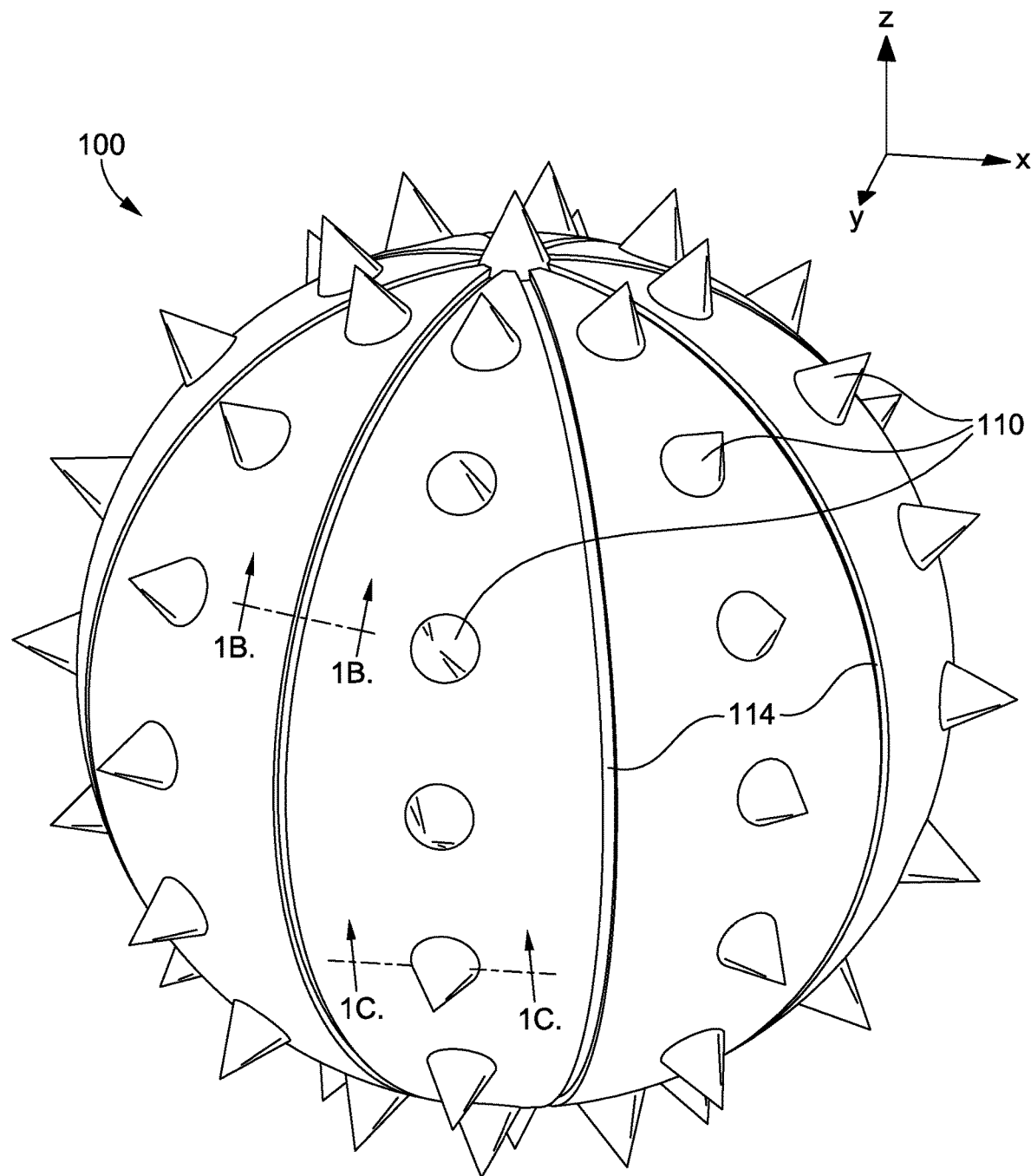
FIG. 1A illustrates a first exemplary brachytherapy device having a three-dimensional shape with protrusions and grooves extending across the surface of the brachytherapy device in accordance with aspects herein.

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As described above, aspects herein are directed to a bioabsorbable and/or biocompatible implantable brachytherapy device and/or stereotactic marker device having a plurality of protrusions and/or grooves useable for anchoring the device within a tumor bed. In one exemplary aspect, radioactive seeds may be positioned within one or more grooves and/or one or more central channels on the brachytherapy device to deliver customizable amounts of radiation to the tumor bed. In an alternative aspect, the radioactive seeds may be positioned within channels of one or more hollow tubes that form the brachytherapy device. When used as a stereotactic marker, radiopaque markers may be positioned within the grooves, central channels, or the tube channels. A description of the brachytherapy devices and/or stereotactic marker devices is provided below with reference to the figures.

As used throughout this disclosure, the term "biocompatible device" means compatible with living tissue such that the biocompatible device is not toxic, is not physiologically reactive and generally does not cause an immunological reaction. The term "bioabsorbable device" as used herein generally means a device that is biocompatible as defined above and that is capable of being absorbed into the patient's body over time.

In exemplary aspects, the brachytherapy devices described herein may be formed from a silicone (polysiloxane) polymer, silastic (polydimethylsiloxane), polyether ether ketones (PEEK), or mixtures of polysiloxane, polydimethylsiloxane, and PEEK. As well, the brachytherapy device described herein may be formed from polyglycolic acid, L polylactic acid, D polylactic acid, or mixtures of L and D polylactic acid. In general, polysiloxane, polydimethylsiloxane, and PEEK may be used to form devices which are biocompatible, and polyglycolic acid and L and/or D polylactic acid may be used to form bioabsorbable devices. The brachytherapy devices described herein may be formed by, for example, 3-D printing, using complementary molds, injection molding, and the like. When the devices are configured to be bioabsorbable, materials may be selected and/or the devices may be configured such that the device absorbs at a rate that is at least four times the half-life of any radioactive seeds/strands positioned on or in the device. For instance, Palladium 103 has a half-life of 17 days. In this instance, materials for the device would be selected and/or the device may be configured so that the device does not completely absorb for at least 68 days. In one example, the amount of the L-isomer of polylactic acid may be increased and the amount of the D-isomer may be decreased to slow the rate of bioabsorption. Conversely, the amount of the L-isomer of polylactic acid may be decreased and the amount of the D-isomer may be increased to increase the rate of bioabsorption.

The term "radioactive seed" as used herein refers to a single radiation source that is positioned within a brachytherapy device. The term "radioactive strand" as used herein refers to multiple radiation sources positioned within a brachytherapy device, where the "strand" may be in the form of an actual strand or tube. Radioactive seeds or strands may comprise low-dose and/or high-dose radiation sources such as, for example, palladium-103, iodine-125, cesium-131, gold-198, radium-223, yttrium-90, iridium-192, and the like. It is contemplated herein that other active elements may be used in association with the brachytherapy devices described herein. An active element is an element that has therapeutic properties for the treatment of a patient, such as, for example, pharmaceutical, nuclear, or radioactive properties. Any and all aspects, and any variation thereof, are contemplated as being within the scope herein.

Aspect 1

With reference first to FIG. 1A, a brachytherapy device 100 is illustrated having a generally solid, three-dimensional (3-D) shape. The brachytherapy device 100 is configured to be permanently placed within a tumor bed at the time of surgical resection of a tumor. The particular shape shown in FIG. 1A is a sphere but it is contemplated herein that the 3-D shape may comprise an ellipsoid shape, a cylindrical shape, and variants thereof. The brachytherapy device 100 may be formed in a number of predetermined sizes such as, for example, about 2 cm, 3 cm, 5 cm, or 7 cm as measured across the maximum diameter of the device 100; the use of different sizes better accommodates different sizes of tumor beds. A brachytherapy device having a 3-D shape, such as the device 100, may be particularly useful in cancers such as breast or brain where the tumor bed generally comprises a three-dimensional shape. Further, because the brachytherapy device 100 comprises a solid 3-D shape, it can be considered a space-occupying device. This may make the device 100 especially useful following a breast lumpectomy. In this case, the placement of a solid, 3-D device having a size corresponding to the size of the tumor bed may help to provide a pleasing aesthetic to the breast following lumpectomy surgery by helping to fill the tumor cavity and preventing or minimizing depressions on the exterior of the breast.

The materials described above for forming the brachytherapy devices described herein may cause the resulting brachytherapy device, such as the brachytherapy device 100, to exhibit a degree of elastic deformability (i.e., a temporary shape change that is self-reversing after a stress is removed). In other words, the device 100, in exemplary aspects, may not be completely rigid. By forming the device 100 to have a degree of elastic deformability, the brachytherapy device 100 may be better adapted to adjust to external pressures. This may be particularly useful when the brachytherapy device 100 is used in breast cancer patients. For example, because the breast is often subject to external pressures, using a device that exhibits some degree of elastic deformability allows the breast to more comfortably adapt to external pressures as opposed to using a rigid device. This, in turn, improves the patient's comfort.

The brachytherapy device 100 comprises a plurality of protrusions 110 extending in a positive z-direction with respect to the surface plane of the device 100. As shown in FIG. 1A with reference to the Cartesian coordinate system, the surface plane of the device 100 at any one location may be thought of as extending in an x direction and a y direction (both positive and negative). The protrusions 110 extending in a positive z-direction would extend outward from the surface plane of the device 100. In exemplary aspects, the protrusions 110 are useable to anchor the brachytherapy device 100 in the tumor bed thereby minimizing or eliminating problems due to migration, motion, rotation, or shift in position after intra-operative placement of the device 100. In one exemplary aspect, the protrusions 110 are uniformly distributed over the surface of the device 100. However, it is contemplated herein that the protrusions 110 may be localized to one or more discrete areas of the device 100. Any and all aspects, and any variation thereof, are contemplated as being within aspects herein.

Figure 1B:
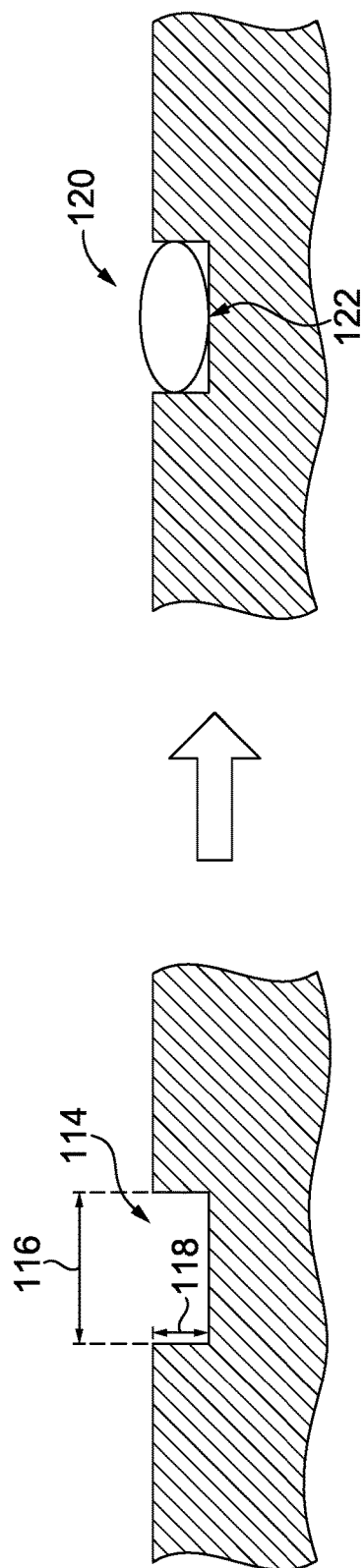
FIG. 1B illustrates a cross-section of a groove without and with a radioactive seed and/or a radiopaque marker positioned therein taken along cut line 1B-1B of FIG. 1A in accordance with aspects herein.
Figure 1C:
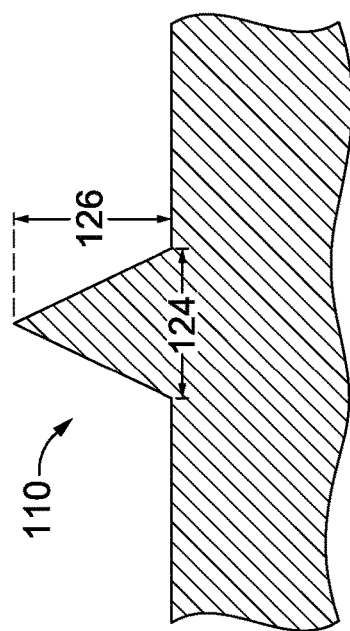
FIG. 1C illustrates a cross-section of a protrusion taken along cut line 1C-1C of FIG. 1A in accordance with aspects herein.

Continuing with respect to the protrusions 110, and with reference to FIG. 1C which depicts a cross-section of a protrusion 110 taken along cut line 1C-1C of FIG. 1A, the protrusions 110 may be integrally formed with the brachytherapy device 100. In other words, they are formed of the same material as the brachytherapy device 100. However, it is also contemplated herein that the protrusions 110 may be formed by adding an additional biocompatible and/or bioabsorbable treatment to the surface of the device 100. Each protrusion 110 has a conical shape with a base width or diameter 124 from about 0.9 mm to about 5.5 mm, or from about 1.0 mm to about 5.0 mm. Further, each protrusion 110 may have a height 126 from about 0.4 mm to about 5.1 mm, or from about 0.5 mm to about 5.0 mm. As used herein, the term "about" means within ±10% of a designated value.

With respect to FIG. 1A, the protrusions 110, in one exemplary aspect, are arranged in rows with each row extending from a first pole of the device 100 to a second opposite pole of the device 100. As such, the protrusions 110 are generally uniformly distributed across the surface of the device 100. Each protrusion 110 may be spaced apart from an adjacent protrusion 110 in a particular row by a distance of from about 1 mm to about 14 mm or from about 2 mm to about 12 mm. It is contemplated herein that the rows of protrusions 110 may not extend all the way from the first pole of the device 100 to the second opposite pole of the device 100 (i.e., the rows of protrusions 110 may extend only partially between the poles of the device 100). It is further contemplated herein that the protrusions 110 may be not be configured in rows but may be randomly positioned on the device 100, and/or arranged in some other pattern other than linear rows (e.g., curvilinear rows, zig-zag rows, sinusoidal rows, and the like). Any and all aspects, and any variation thereof, are contemplated as being within aspects herein.

With continued reference to FIG. 1A and with further reference to FIG. 1B, which depicts a cross-section of a groove taken along cut line 1B-1B of FIG. 1A, the brachytherapy device 100 further comprises a plurality of grooves 114 extending in a negative z-direction with respect to the surface plane of the device 100. That is, the grooves 114 extend inwardly with respect to the surface plane of the device 100. As shown in FIG. 1B, the grooves 114 are useable to hold in place loose radioactive seeds, radioactive strands, radiopaque markers, and/or other active elements 120. For example, the seeds, strands, markers, or active elements 120 may be positioned within the grooves 114 and held in place through the use of a medical adhesive such as n-2-butyl-cyanoacrylate. As well, because the device 100 may exhibit some elastic deformability, the seeds, strands, markers, or active elements 120 may be biased or tensioned into the grooves 114 and held in place through the elastic tension created by the biasing process. This may eliminate the need to use a medical adhesive in some exemplary aspects.

In general, loose radioactive seeds have a diameter of about 0.8 mm, while radioactive strands (radioactive seeds positioned within a tube of bioabsorbable material) have a diameter of about 0.99 mm. With this as context, and with respect to FIG. 1B, the grooves 114 may have a width 116 from about 0.75 mm to about 0.9 mm and a depth 118 from about 1.0 mm to about 1.2 mm when configured for use with loose radioactive seeds. Alternatively, the grooves 114 may have a width 116 from about 0.95 mm to about 1.1 mm and a depth 118 from about 1.0 mm to about 1.2 mm when configured for use with radioactive strands. It is contemplated herein that the brachytherapy device 100 may have some grooves 114 configured for loose radioactive seeds and some grooves 114 configured for radioactive strands. Any and all aspects, and any variation thereof, are contemplated as being within aspects herein.

Continuing, the grooves 114, in one exemplary aspect, are configured to extend from the first pole of the device 100 to the second opposite pole of the device 100. As such, the grooves 114, like the protrusions 110, are generally uniformly distributed across the surface of the device 100. In one exemplary aspect, the rows of protrusions 110 alternate with the grooves 114 to form a repeating pattern of "row of protrusions-groove-row of protrusions-groove," and the like. However, it is contemplated herein that there may be other patterns such as two grooves separated by a row of protrusions, two rows of protrusions separated by a groove, and the like. It is contemplated herein that the grooves 114 may not extend all the way from the first pole of the device 100 to the second opposite pole of the device 100 (i.e., the grooves 114 may extend only partially between the poles of the device 100). It is further contemplated herein that the grooves 114 may be randomly positioned on the device 100, and/or arranged in some other pattern than that shown in FIG. 1A (e.g., curvilinear, zig-zag, sinusoidal, and the like). Any and all aspects, and any variation thereof, are contemplated as being within aspects herein.

Figure 4A:
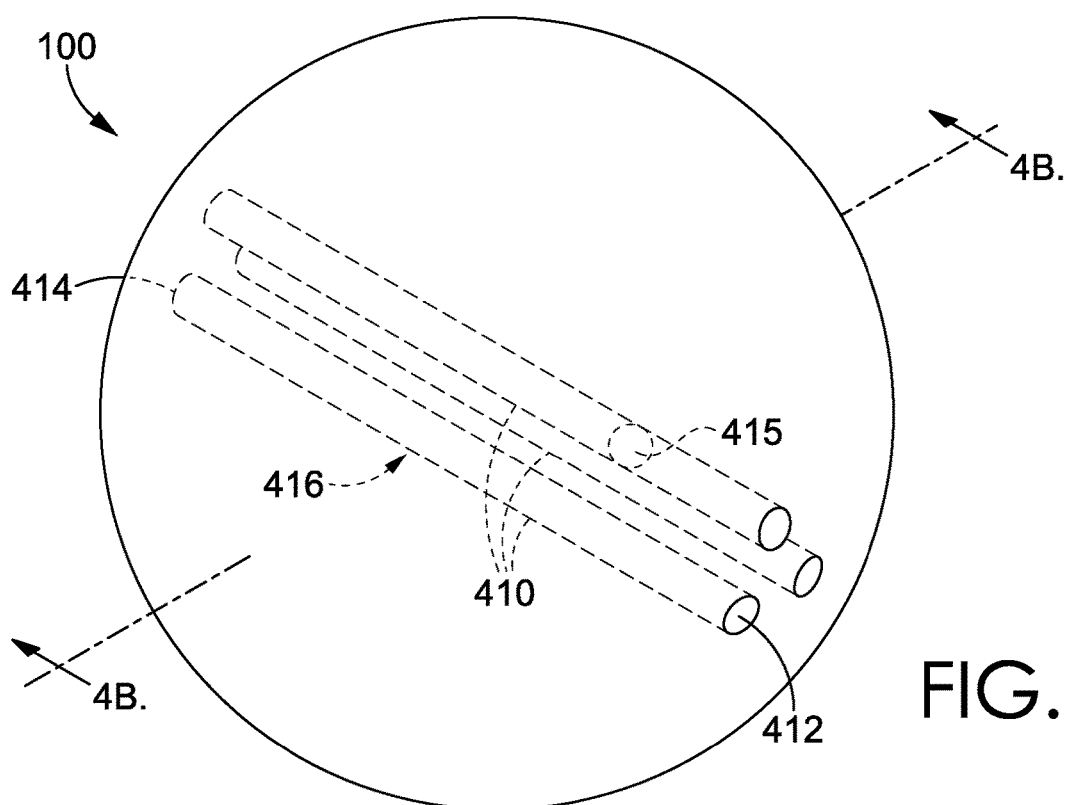
FIG. 4A illustrates exemplary central channels of the brachytherapy device of FIG. 1A in accordance with aspects herein.
Figure 4B:
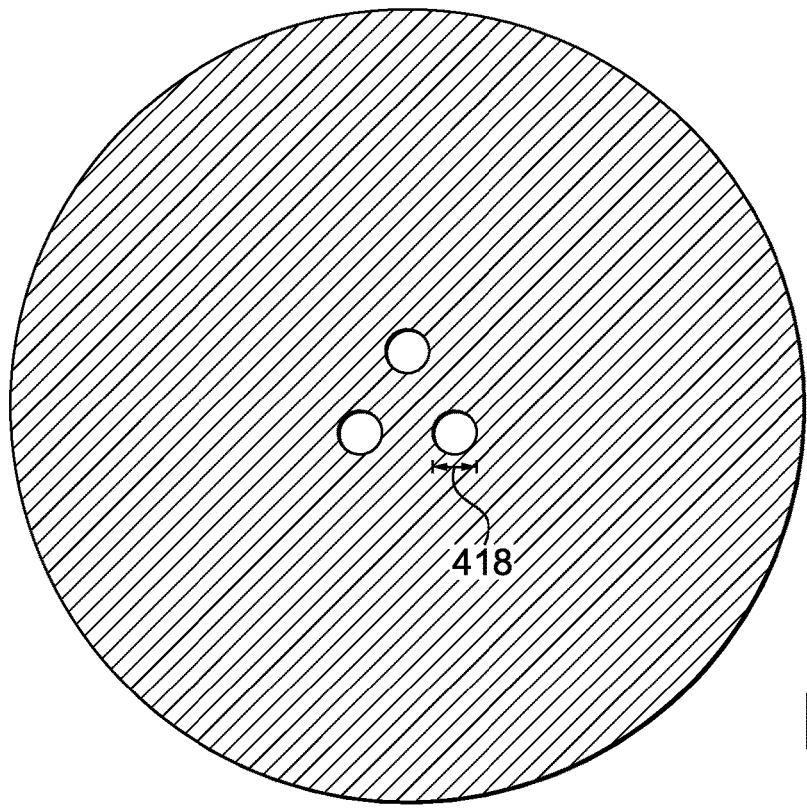
FIG. 4B illustrates a cross-section of the exemplary central channels of FIG. 4A taken along cut line 4B-4B in accordance with aspects herein.

As shown in FIG. 4A, which depicts the device 100 without any protrusions or grooves for illustrative purposes, and as further shown in FIG. 4B, which depicts a cross-section of the device 100 taken across cut line 4B-4B of FIG. 4A, the device 100 may optionally comprise one or more central channels 410 that extend through the body of the device 100. With respect to FIG. 4A in particular, a central channel, such as central channel 416, may extend from a first surface location 412 on one side the device 100, through the body of the device 100, to a second surface location 414 on the device 100 where the second surface location 414 is opposite the first surface location 412. The central channels 410 thereby form through passages in the device 100 as shown in FIG. 4B. In one exemplary aspect, one or more of the central channels 410 may be configured to pass through a maximum diameter of the device 100. The central channels 410 may number from about 1 to 12 and may have a diameter 418 from about 0.7 mm to about 1.2 mm, or from about 0.8 mm to about 1.1 mm.

The central channels 410 are useable for additional seed, strand, radiopaque marker, and/or active element placement. Similar to the grooves, the radioactive seeds/strands/markers/elements may be held in the central channels 410 via a medical adhesive, or the radioactive seeds/strands/markers/elements may be biased into the central channels 410 and held in place via the elastic tension created by the biasing process. In one exemplary aspect, high dose radiation seeds, such as seed 415 in FIG. 4A, may be placed in one or more of the central channels 410 while low dose radiation seeds may be positioned in the grooves 114. Because the central channels 410 are positioned further away from the tumor bed as compared to the grooves 114, some of the damaging effects of the higher dose radiation seeds may be lessened based on the inverse-square law which generally states that the intensity of the radiation is inversely proportional to the square of the distance from the radioactive source. It is also contemplated herein that low dose radiation seeds may also be placed in the central channels 410. Any and all aspects, and any variation thereof, are contemplated as being within aspects herein.

Figure 2A:
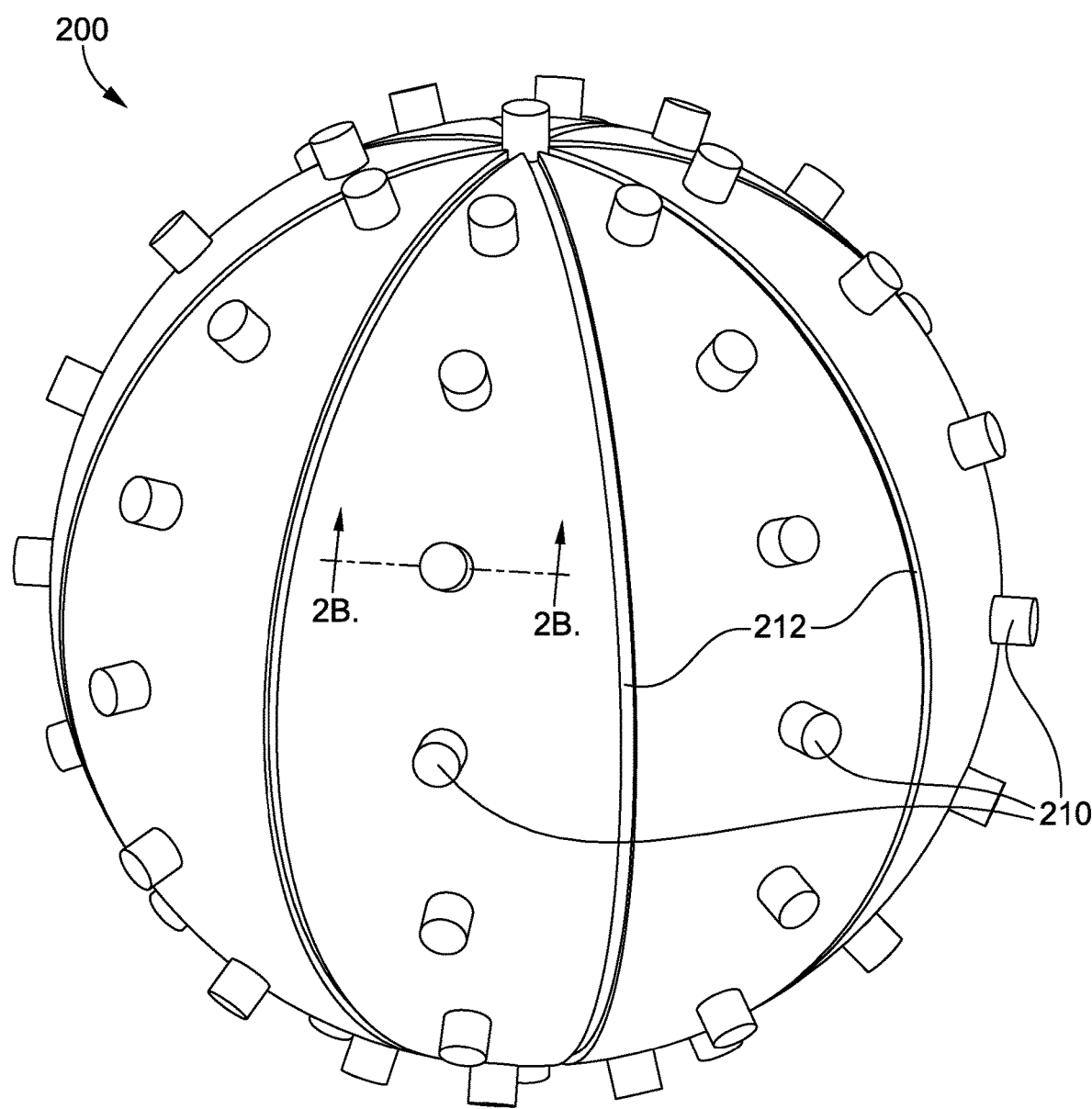
FIG. 2A illustrates a second exemplary brachytherapy device having a three-dimensional shape with protrusions and grooves extending across the surface of the brachytherapy device in accordance with aspects herein.
Figure 2B:
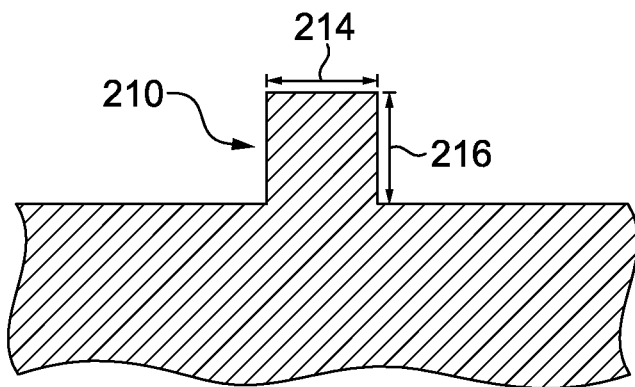
FIG. 2B illustrates a cross-section of a protrusion taken along cut line 2B-2B of FIG. 2A in accordance with aspects herein.

FIG. 2A illustrates another exemplary brachytherapy device 200 in accordance with aspects herein. The device 200 shares the same features as the device 100 including grooves 212 and protrusions 210 and optionally central channels. The main difference between the device 200 as compared to the device 100 is that the protrusions 210 have a generally cylindrical shape as opposed to a conical shape as in FIG. 1. In this exemplary aspect, and as shown in FIG. 2B which represents a cross-section of a protrusion 210 taken along cut line 2B-2B of FIG. 2A, the protrusions 210 may have a uniform width or diameter 214 from about 0.9 mm to about 5.5 mm, or from about 1.0 mm to about 5.0 mm and a height 216 from about 0.4 mm to about 5.1 mm, or from about 0.5 mm to about 5.0 mm.

Figure 3A:
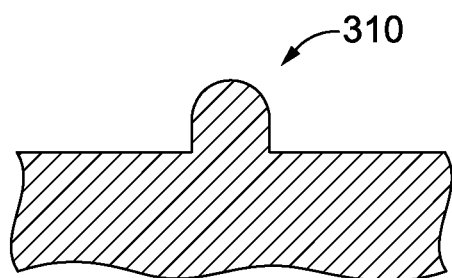
FIGS. 3A-3C illustrate some exemplary cross-sectional shapes of protrusions in accordance with aspects herein.
Figure 3B:
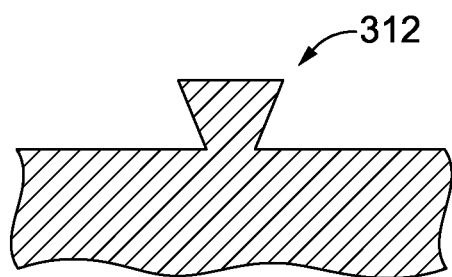
Figure 3C:
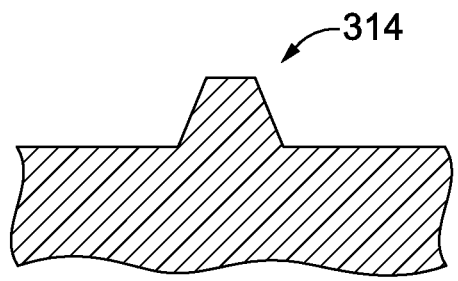

It is contemplated herein that the device 100 or the device 200 (or any of the other devices described herein) may have other shape configurations for the protrusions. FIGS. 3A-3C illustrate some additional exemplary shapes. For example, FIG. 3A depicts a protrusion 310 having a semi-hemispherical shape. FIG. 3B depicts a protrusion 312 having a planar distal surface that comprises a greater surface area than the base of the protrusion 312 (i.e., the protrusion 312 expands outward), while FIG. 3C depicts a protrusion 314 having a planar distal surface that comprises a smaller surface area than the base of the protrusion 314 (i.e., the protrusion 314 tapers as it extends outward). Additional shape configurations beyond those shown are contemplated as being within aspects herein.

Aspect 2

Figure 5A:
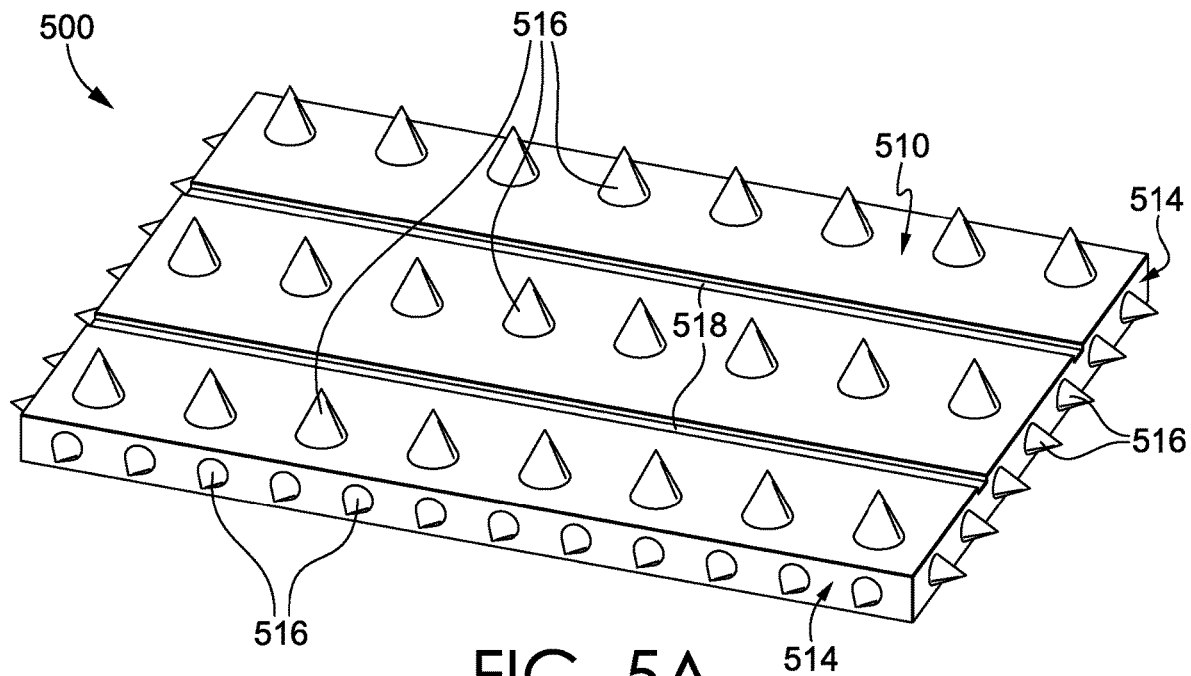
FIG. 5A illustrates a first surface of a third exemplary brachytherapy device having a two-dimensional shape with protrusions and grooves in accordance with aspects herein.
Figure 5B:
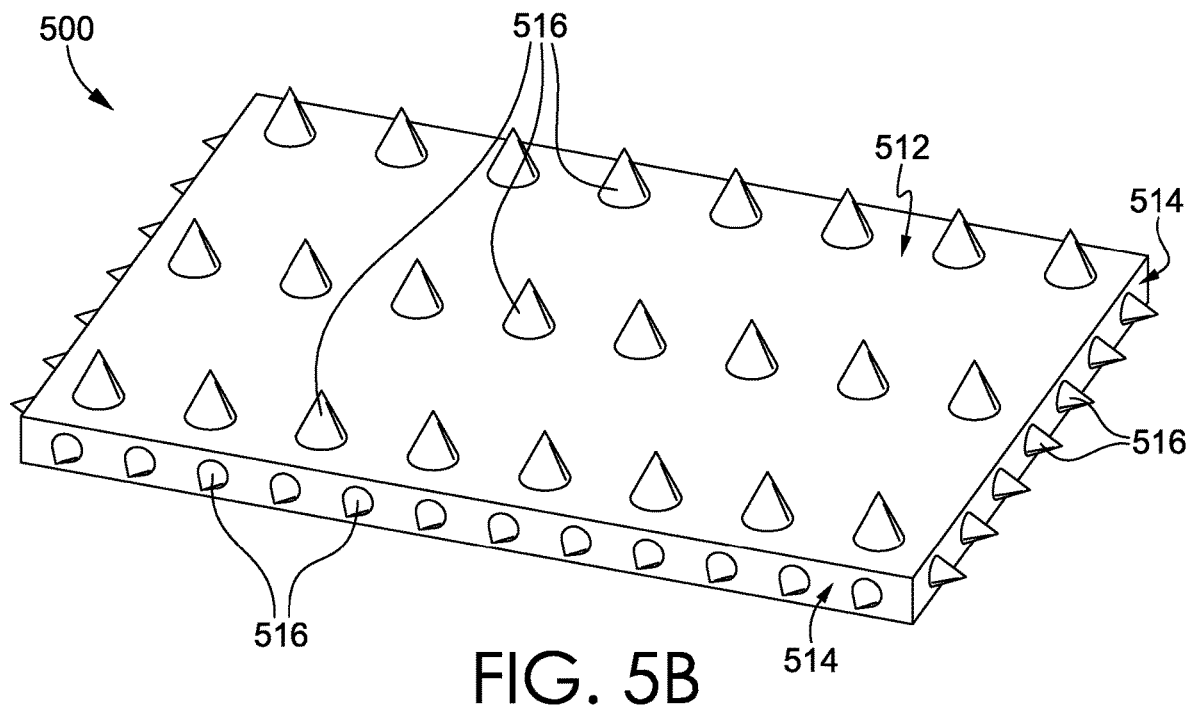
FIG. 5B illustrates a second opposite surface of the third brachytherapy device of FIG. 5A in accordance with aspects herein.

Turning now to FIGS. 5A and 5B, a brachytherapy device 500 is shown as having a generally two-dimensional (2-D)

planar shape comprising a first planar surface 510 shown in FIG. 5A, and a second planar surface 512 opposite the first planar surface 510 shown in FIG. 5B. The device 500 further comprises one or more sides 514 extending between, and generally perpendicular to, the first planar surface 510 and the second planar surface 512. In exemplary aspects, the sides 514 may have a height from about 2.0 mm to about 4.0 mm. In other words, the device 500 may have a thickness from about 2.0 mm to about 4.0 mm. The use of a device having a 2-D planar shape may be especially useful in tumors such as sarcomas where the tumor bed generally comprises a one-dimensional planar surface.

Although the brachytherapy device 500 is shown in a rectangular form, the device 500 may also comprise a square form. When the device 500 is in the form of a square, the device 500 may be formed in a number of predetermined sizes such as about 2×2 cm, 4×4 cm, 6×6 cm, 8×8 cm, or 10×10 cm. When the device 500 is in the form of a rectangle, the device 500 may be formed in a number of predetermined sizes such as about 2×4 cm, 2×6 cm, 4×6 cm, 4×8 cm, 4×10 cm, 6×8 cm, or 6×10 cm. It is also contemplated herein that the device 500 may be formed into other shapes such as a 2-D planar circle, a 2-D planar ellipse, and the like. It is further contemplated herein that the device 500 may be cut to shape or formed to shape at the time of intra-operative placement. This may be useful for tumor beds having an irregular shape. Any and all aspects, and any variation thereof, are contemplated as being within aspects herein.

In one exemplary aspect, the device 500 may comprise a plurality of protrusions 516 useable for anchoring the device 500 in a tumor bed. The plurality of protrusions 516 may extend in a positive z-direction from, for example, the first planar surface 510, the sides 514, and the second planar surface 512 of the device 500 and may be integrally formed from the same materials used to form the device 500. Alternatively, the protrusions 516 may be formed by adding an additional biocompatible or bioabsorbable treatment to the surface of the device 500. The protrusions 516 may be conical in shape and may have similar dimensions as those described for the protrusions 110 of the device 100. Alternatively, the protrusions 516 may have a cylindrical shape such as that shown for the device 200 or may have one of the shape configurations shown in FIGS. 3A-3C. In one exemplary aspect, the protrusions 516 may be arranged in linear rows along the first planar surface 510, along the sides 514, and along the second planar surface 512, where the rows extend from a first end of the device 500 to a second end of the device 500. Although linear rows of protrusions 516 are shown for the device 500, it is contemplated herein that the protrusions 516 may be randomly positioned on the device 500 or may assume other patterns than those shown (e.g., curvilinear rows, zig-zag rows, sinusoidal rows, and the like). Moreover, it is contemplated herein that the rows of protrusions 516 may not extend all the way to the first and second ends of the device 500. Any and all aspects, and any variation thereof, are contemplated as being within aspects herein.

The device 500 may further comprise a plurality of grooves 518 having similar dimensions as those described for the grooves 114 of the device 100 where the grooves 518 are useable for securing radioactive seeds, strands, radiopaque markers, and/or active elements. Although only two grooves 518 are shown, it is contemplated herein that the device 500 may comprise any number of grooves. In exemplary aspects, the grooves 518 may be positioned on just the first planar surface 510, where the first planar surface 510 is configured to be positioned adjacent to the tumor bed when placed intra-operatively. It is also contemplated herein that the grooves 518 may be positioned on the second planar surface 512 and/or along one or more of the sides 514 of the device 500. In one exemplary aspect, the grooves 518 extend from a first end of the device 500 to a second end of the device 500 along its longitudinal axis. However, it is contemplated herein that the grooves 518 may extend only partially between the first and second ends of the device 500 or may extend widthwise across the device 500 when the device 500 comprises a rectangular shape. Although the grooves 518 are shown as being linear in form, it is contemplated herein that the grooves 518 may comprise other shapes such as curvilinear, sinusoidal, zig-zag, and the like. Any and all aspects, and any variation thereof, are contemplated as being within aspects herein. Similar to the device 100, a particular groove 518 may alternate with a row of protrusions 516 to form a repeating pattern. It is contemplated herein that the grooves 518 and the protrusions 516 may assume other patterns as well such as, for example, groove-groove-row of protrusions, and the like.

Aspect 3

Figure 6A:
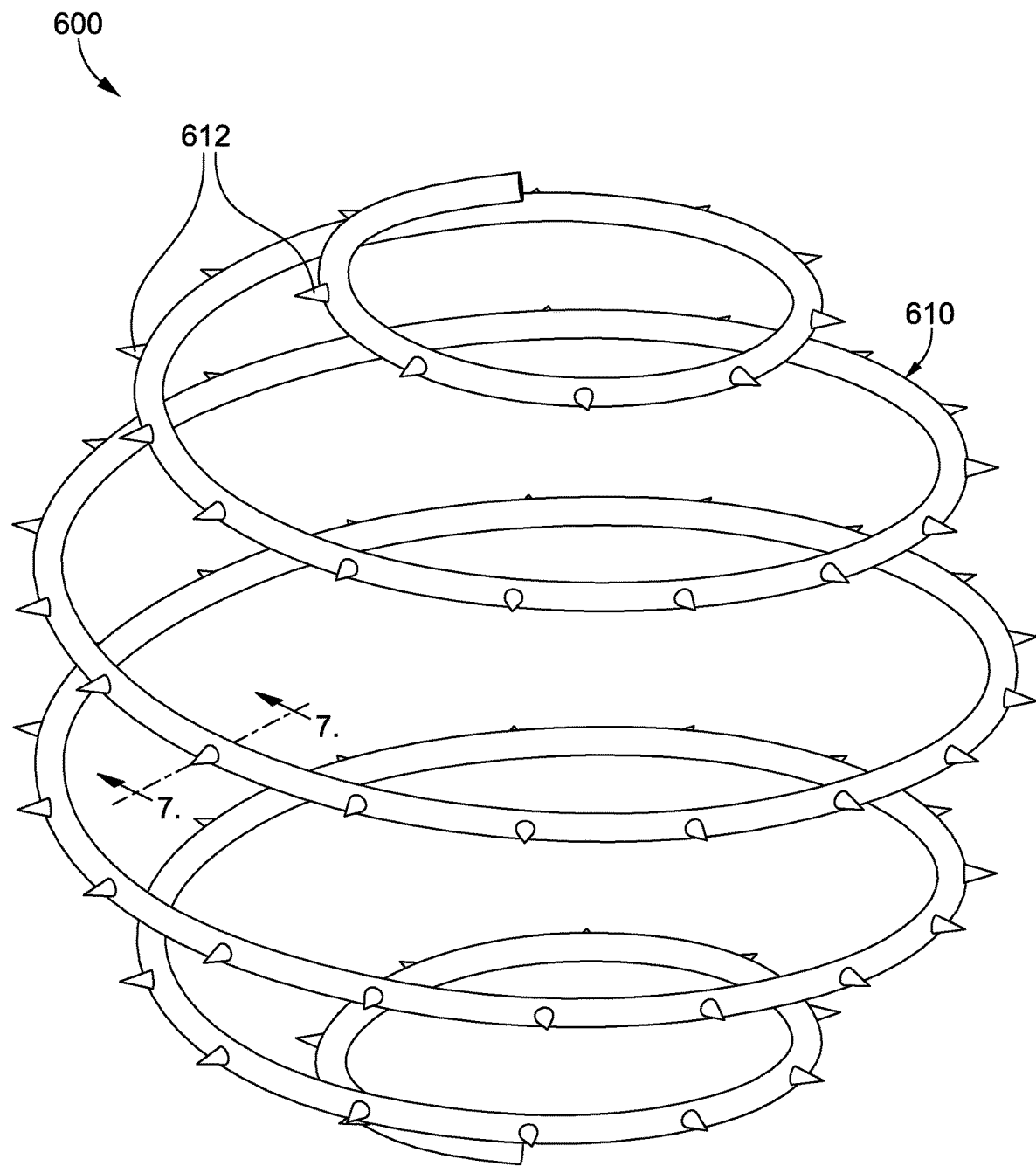
FIG. 6A illustrates a fourth exemplary brachytherapy device having a helical shape formed form a single, continuous hollow tube and further having protrusions in accordance with aspects herein.

FIG. 6A illustrates another brachytherapy device 600 in accordance with aspects herein. The device 600 comprises a single, continuous, hollow tube 610 formed into a helix having a spherical shape as shown. It is also contemplated herein that the tube 610 may be formed into other shapes such as a cylindrical shape, an ellipsoid shape, a disc shape, and the like. The device 600 may come in a number of predetermined sizes such as sizes having a diameter of about 2 cm, 3 cm, 5 cm, or 7 cm.

As described above, features of the device 600 such as material composition or device configuration may be altered to increase or decrease the time it takes for the device 600 to bioabsorb. In one example, a thickness of the walls forming the tube 610 may be increased to slow the rate of bioabsorption, and a thickness of the walls may be decreased to increase the rate of bioabsorption. Additionally, or alternatively, the percentage of, for instance, the D-isomer of polylactic acid or the L-isomer of polylactic acid may be increased or decreased to alter the rate of bioabsorption.

Continuing, because of its helical form, the device 600 has a vacancy at its center. That is, the device 600 is generally a non-space occupying (or minimally-space occupying) device. Since it generally occupies less space as compared to, for instance, the device 100, this configuration may be useful for placement in tumor beds where an increase in pressure is generally avoided (e.g., brain tumors). Moreover, the vacancy at the center of the device 600 may also act as a repository for any accumulation of bloods, secretions, and inflammatory fluids thereby preventing or minimizing the buildup of these materials in the space between the device 600 and the tissue of the tumor bed. This may help to improve the efficacy of the device 600 by allowing the radioactive seeds/strands to be positioned closer to the tumor bed.

In exemplary aspects, the tube 610 has a continuous, central channel (i.e., bore) 711 extending at least partially or completely along the length of the tube 610 where the channel 711 is useable for receiving radioactive seeds, strands, radiopaque markers, and/or active elements. This aspect is shown in FIGS. 7 and 8 where FIG. 7 depicts a cross-section of the tube 610 taken along cut line 7-7 of FIG. 6A, and FIG. 8 depicts a longitudinal cross-section of the tube 610. As shown in FIGS. 7 and 8, the outer diameter 710 of the tube 610 may be from about 3.0 mm to about 9.0 mm, or from about 4.0 mm to about 8.0 mm. And a diameter 712 of the channel 711 located in the tube 610 is from about 1.1 mm to about 1.5 mm, or from about 1.2 mm to about 1.4 mm.

Continuing, the tube 610 may have at least one open end in which radioactive seeds, radioactive strands, radiopaque markers, and/or active elements may be placed and secured using, for example, a medical adhesive at the time of placement in the tumor bed. With respect to this aspect, the open end of the tube 610 may be secured using, for example, a clip, a plug, a medical adhesive, and the like. Alternatively, the tube 610 may be pre-loaded with radioactive seeds, strands, radiopaque markers, and/or active elements during manufacturing. When pre-loaded, the tube ends may be sealed prior to shipping. With respect to FIG. 8, the channel 711 extends along at least a portion of the length of the tube 610 and is useable for receiving seeds, strands, markers, and/or active elements as shown by reference numeral 810 in FIG. 8. It is also contemplated herein that the channel 711 extends along an entire length of the tube 610. Any and all aspects, and any variation thereof, are contemplated as being within aspects herein.

Returning to FIG. 6A, in one exemplary aspect, the device 600 comprises a plurality of conical protrusions 612 extending in a positive z-direction with respect to the surface plane of the tube 610. The protrusions 612 have similar dimensions as to those described for the device 100 or the device 500. Alternatively, the protrusions 612 may have a cylindrical form as depicted for the device 200, or the protrusions 612 may comprise other configurations such as those shown in FIGS. 3A-3C. In exemplary aspects, the protrusions 612 are configured to extend away from the center of the device 600. To describe this differently, the protrusions 612 may be positioned on just one side of the tube 610—the side that faces away from the center of the device 600 (also known as the outer-facing surface of the tube 610). It is also contemplated herein that the protrusions 612 may be positioned on the tube 610 such that they extend both away from the center of the device 600 and toward the center of the device 600. Any and all aspects, and any variation thereof, are contemplated as being within aspects herein. Similar to the devices already described, the protrusions 612 are configured to anchor the device 600 in, for example, a tumor bed to minimize migration, rotation, or shifting of the device 600.

Figure 6B:
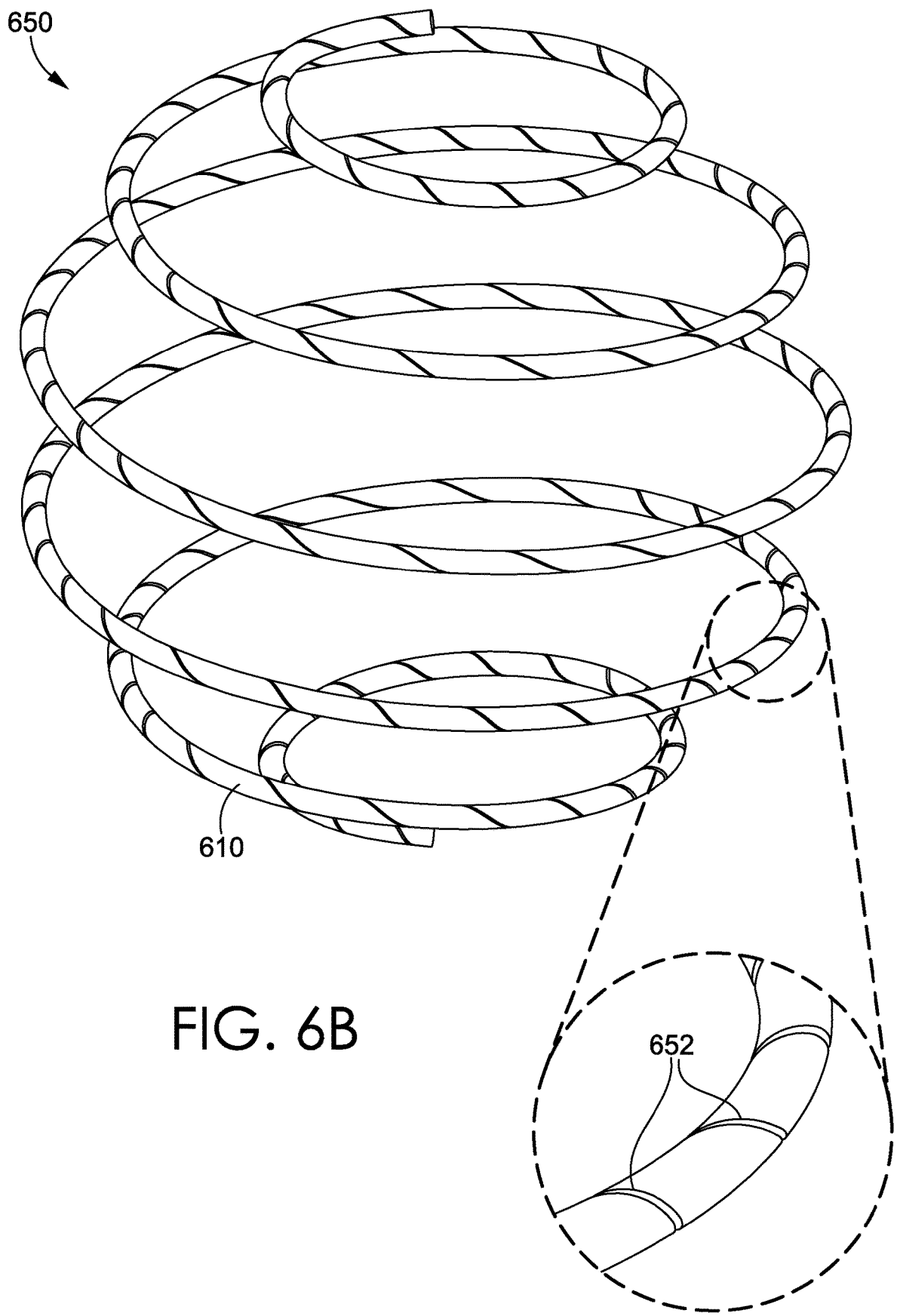
FIG. 6B illustrates an alternative configuration of the fourth exemplary brachytherapy device having grooves instead of protrusions in accordance with aspects herein.

FIG. 6B depicts a brachytherapy device 650 having a similar configuration as the brachytherapy device 600 but having grooves 652 instead of protrusions, where the grooves 652 are useable for anchoring the brachytherapy device 650. As shown in the magnified view, the grooves 652 extend in a negative z-direction with respect to the surface plane of the tube 610. Each groove 652 may have a width from about 0.1 mm to about 2.0 mm, and each groove 652 may have a depth from about 0.1 mm to about 2.0 mm. In exemplary aspects, the grooves 652 may be rotationally positioned along the tube 610. To state it differently, the grooves 652 may extend in a helical fashion or a corkscrew manner along the length of the tube 610. However, it is contemplated that the grooves 652 may be arranged in other patterns on the tube 610 and may extend only partially along the length of the tube 610. The grooves 652 contribute to making the outer surface of the tube 610 irregular or rough which, in turn, helps to anchor the device 650 in the tumor bed. For example, the grooves 652 may help to promote tissue ingrowth thereby helping to anchor the device 650. It is further contemplated herein that other features besides grooves may be used to create a rough outer surface of the tube 610. For example, the outer surface of the tube 610 may be molded or formed to have ridges, braids, or some other type of texture. In another aspect, an additional bioabsorbable or biocompatible treatment may be applied to the outer surface of the tube 610 to create the rough surface. Any and all aspects, and any variation thereof, are contemplated as being within aspects herein.

Aspect 4

Figure 9A:
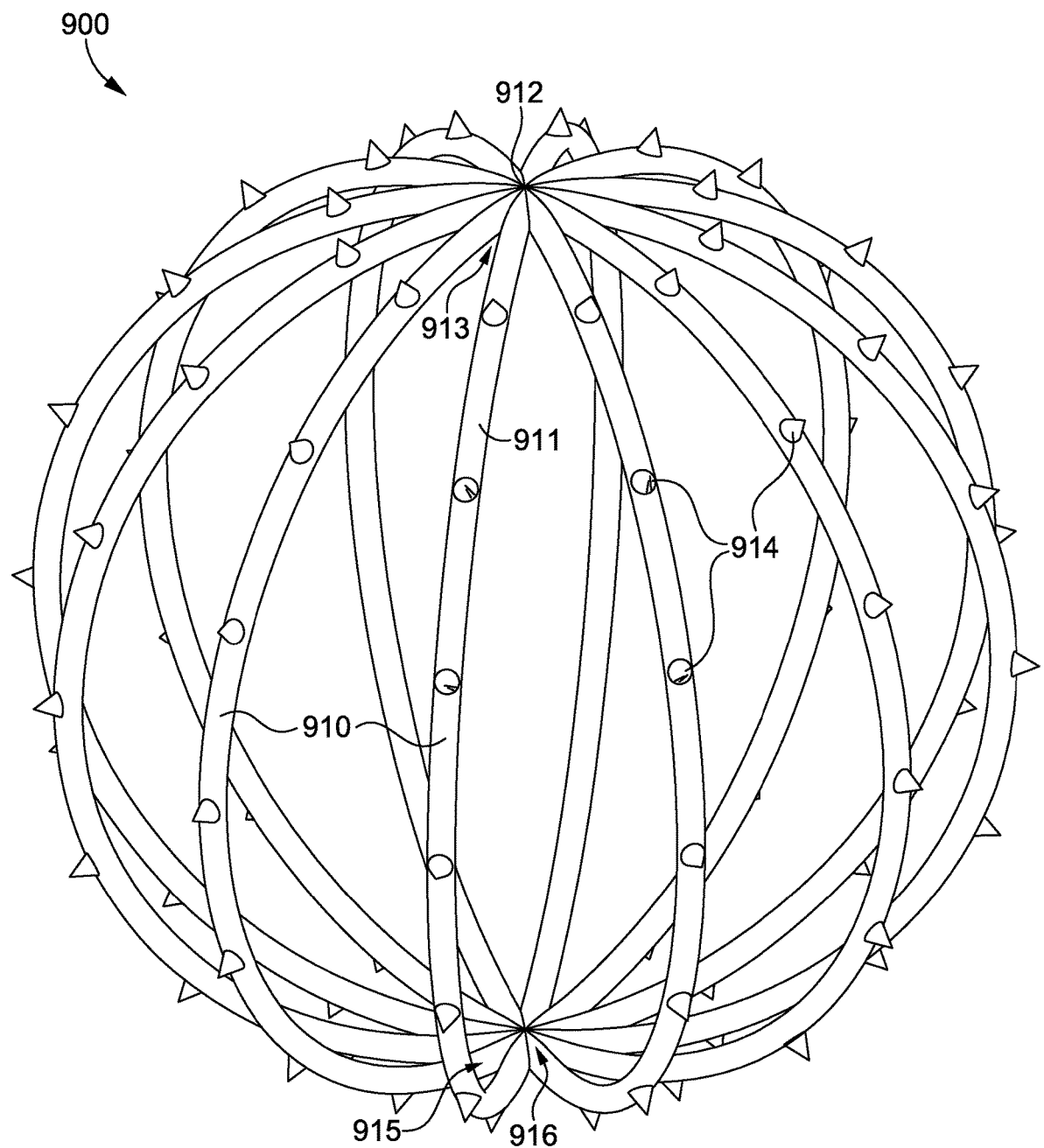
FIG. 9A illustrates a fifth exemplary brachytherapy device having a spherical shape and formed from a plurality of hollow tubes and further having protrusions in accordance with aspects herein.

FIG. 9A illustrates a brachytherapy device 900 in accordance with aspects herein. The device 900 comprises a plurality of hollow tubes 910 that are formed into a spherical shape having a first pole 912 and a second opposite pole 916. Although shown in a spherical shape, it is contemplated herein that the device 900 may comprise other shapes such as a 3-D ellipsoid shape, a 3-D cylindrical shape, a 2-D disc shape, and the like. Similar to the device 600, the device 900 may be formed in such a way as to increase or decrease the time it takes for the device 900 to bioabsorb. For example, a thickness of the walls forming the tubes 910 may be increased to slow the rate of bioabsorption, and a thickness of the walls may be decreased to increase the rate of bioabsorption. Additionally, or alternatively, the percentage of, for instance, the D-isomer of polylactic acid or the L-isomer of polylactic acid may be increased or decreased to alter the rate of bioabsorption.

The device 900 may be formed using the same materials as described with respect to the devices 100, 200, 500, 600, or 650 and, as such, may be biocompatible and/or bioabsorbable and may exhibit a degree of elastic deformation. Similar to the devices 600 and 650, the device 900 has a vacancy at its center. That is, the device 900 is generally a non-space occupying (or minimally-space occupying) device. Because of this, the device 900 may have the same functional advantages as detailed for the devices 600 and 650.

The device 900 may be manufactured in a number of predetermined sizes having diameters such as about 2 cm, 3 cm, 5 cm, or 7 cm. With respect to the device 900, each tube 910, such as tube 911, comprises a first end 913 and a second end 915, and an intervening portion extending between the first end 913 and the second end 915. In exemplary aspects, the respective first ends of the tubes 910 are interconnected at the first pole 912, and the respective second ends of the tubes 910 are interconnected at the second pole 916. This may be accomplished through, for example, a molding process or a 3-D printing process. In exemplary aspects, the intervening portions of the tubes are spaced apart from one another by a predetermined distance such as from about 0.05 mm to about 11 mm, or from about 1 mm to about 10 mm.

Each of the tubes 910 has a continuous, central channel (i.e., bore) extending at least partially along or completely along the length of the respective tube 910. A cross-section of one of the tubes 910 would be similar to that shown in FIG. 7, and a longitudinal cross-section of one of the tubes 910 would be similar to that shown in FIG. 8. In exemplary aspects, the outer diameter of the tubes 910 is from about 3.0 mm to about 9.0 mm, or from about 4.0 mm to about 8.0 mm. And the diameter of the channel located in the respective tubes 910 is from about 1.1 mm to about 1.5 mm, or from about 1.2 mm to about 1.4 mm. The tubes 910 may have at least one open end in which radioactive seeds, radioactive strands, radiopaque markers, and/or active elements may be placed and secured using, for example, a medical adhesive at the time of intra-operative placement. Similar to the devices 600 and 650, the open ends of the tubes 910 may be secured using, for example, a clip.

Alternatively, the tubes 910 may be pre-loaded with radioactive seeds, strands, radiopaque markers, and/or active elements during manufacturing and the open ends of the tubes 910 may be sealed prior to shipping.

In exemplary aspects, one or more of the tube channels may be left empty (i.e., not loaded with a radioactive seed or strand) to protect nearby structures once the brachytherapy device 900 is implanted in the tumor bed. For instance, when used after a breast lumpectomy, tube channels not containing a radioactive seed or strand may be positioned in the tumor bed so as to be adjacent to, for instance, the chest wall, as opposed to the tumor bed. This may help to lessen the effects of radiation on these structures.

In one exemplary aspect and as shown in FIG. 9A, the device 900 comprises a plurality of conical protrusions 914 extending in a positive z-direction with respect to the surface plane of the tubes 910. The protrusions 914 have similar dimensions as to those described for the device 100. Alternatively, the protrusions 914 may have a cylindrical form as depicted for the device 200 or may assume other shape configurations such as those shown in FIGS. 3A-3C. In exemplary aspects, the protrusions 914 are configured to extend away from the center or middle of the device 900. Similar to the devices already described, the protrusions 914 are configured to anchor the device 900 in, for example, a tumor bed to minimize migration or shifting of the device 900.

Figure 9B:
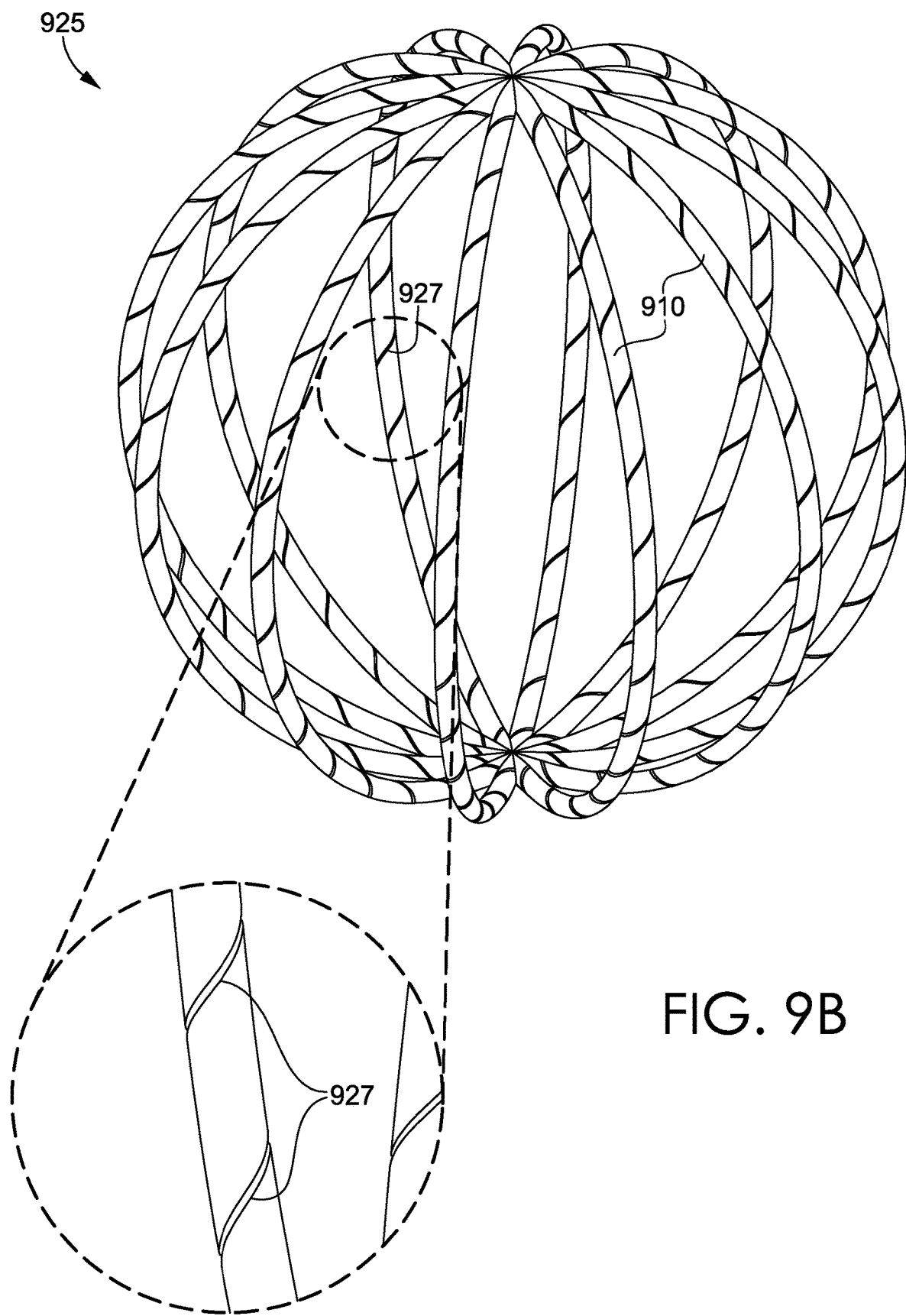
FIG. 9B illustrates an alternative configuration of the fifth exemplary brachytherapy device having grooves instead of protrusions in accordance with aspects herein.

An alternative configuration where grooves are used instead of protrusions is shown in FIG. 9B. FIG. 9B illustrates a device 925 with grooves 927 that are useable for anchoring the brachytherapy device 925. Similar to what was discussed with respect to the device 650, the grooves 927 extend in a negative z-direction with respect to the surface plane of the tubes 910. Each groove 927 may have a width from about 0.1 mm to about 2.0 mm, and each groove 927 may have a depth from about 0.1 mm to about 2.0 mm. In exemplary aspects, the grooves 927 may be rotationally positioned along the tubes 910. To state it differently, the grooves 927 may extend in a helical fashion or a corkscrew manner along the length of the tubes 910. However, it is contemplated that the grooves 927 may be arranged in other patterns on the tubes 910 or may extend only partially along the length of the tubes 910. The grooves 927 contribute to making the outer surface of the tubes 910 irregular or rough which, in turn, helps to anchor the device 925 in the tumor bed. For example, the grooves 927 may help to promote tissue ingrowth thereby helping to anchor the device 925. It is further contemplated herein that other features besides grooves may be used to create a rough outer surface of the tubes 910. For example, the outer surface of the tubes 910 may be molded or formed to have ridges, braids, or some other type of texture. In another aspect, an additional bioabsorbable or biocompatible treatment may be applied to the outer surface of the tubes 910 to create the rough surface. Any and all aspects, and any variation thereof, are contemplated as being within aspects herein.

Figure 9C:
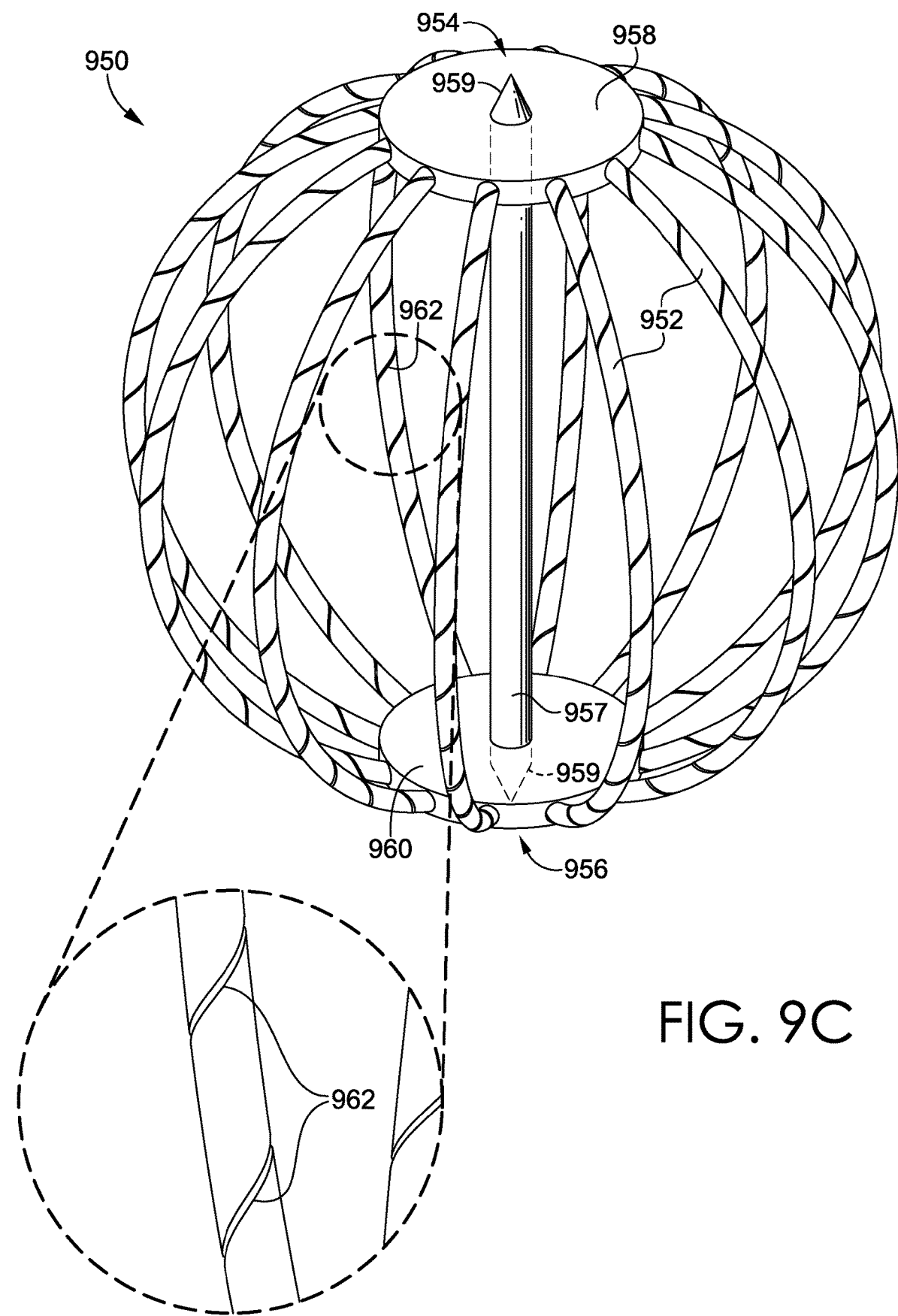
FIG. 9C illustrates an alternative configuration of the fifth exemplary brachytherapy device having a central column, hubs, and grooves in accordance with aspects herein.

Yet another alternative exemplary configuration is shown in FIG. 9C in accordance with aspects herein. Similar to the devices 900 and 925, the device 950 comprises a plurality of hollow tubes 952 that are formed into a spherical shape having a first pole 954 and a second opposite pole 956. The device 950 further comprises a central column 957 that extends through the center of the device 950 and terminates in a first planar hub 958 at the first pole 954 and a second planar hub 960 at the second pole 956. In exemplary aspects, the central column 957 provides additionally stability to the device 950.

Continuing, in a first aspect, the central column 957 may comprise a continuous channel or bore extending partially or completely along the length of the central column 957. A cross-section of the central column 957 in accordance with the first aspect would be similar to that shown in FIG. 7 (minus the protrusion 612), and a longitudinal cross-section of the central column 957 would be similar to that shown in FIG. 8 (minus the protrusions 612). With respect to this aspect, the channel may be useable for receiving a radioactive seed, radioactive strand, radiopaque marker, and/or active element. In a second aspect, the central column 957 may be solid (i.e., not comprising a channel). Any and all aspects, and any variation thereof, are contemplated as being within aspects herein. In exemplary aspects, the central column 957 has a length generally equal to or slightly greater than the diameter of the device 950. For instance, if the diameter of the device comprises about 3 cm, the central column may have a length from about 3.0 cm to about 3.5 cm, from about 3.0 cm to about 3.3 cm, or from about 3.0 cm to about 3.1 cm. Further, in exemplary aspects, the central column 957 may be capped with or may terminate in an optional protrusion 959 at each respective end of the column 957, where the protrusion 959 is useable for helping to anchor the device 950.

Continuing, each of the tubes 952 has a continuous, central channel (i.e., bore) extending at least partially or completely along the length of the respective tube 952. A cross-section of one of the tubes 952 would be similar to that shown in FIG. 7 (minus the protrusion 612), and a longitudinal cross-section of one of the tubes 952 would be similar to that shown in FIG. 8 (minus the protrusions 612). In exemplary aspects, the outer diameter of the tubes 952 is from about 3.0 mm to about 9.0 mm, or from about 4.0 mm to about 8.0 mm. And the diameter of the channel located in the respective tubes 952 is from about 1.1 mm to about 1.5 mm, or from about 1.2 mm to about 1.4 mm. The channel of the tubes 952 is useable to receive a radioactive seed and/or strand, a radiopaque marker, and/or an active element.

Instead of having protrusions extending from the surface of the tubes 952 as described for the device 900, the tubes 952 may instead comprise grooves 962 similar to the brachytherapy device 925. The grooves 962 extend in a negative z-direction with respect to the surface plane of the tubes 952. In exemplary aspects, the grooves 962 may be rotationally positioned along the tubes 952. To state it differently, the grooves 962 may extend in a helical fashion or a corkscrew manner along the length of the tubes 952. However, it is contemplated that the grooves 962 may be arranged in other patterns on the tubes 952 and may extend only partially along the length of the tubes 952. The grooves 962 contribute to making the outer surface of the tubes 952 irregular or rough which, in turn, helps to anchor the device 950 in the tumor bed. For example, the grooves 962 may help to promote tissue ingrowth thereby helping to anchor the device 950. It is further contemplated herein that other features besides grooves may be used to create a rough outer surface of the tubes 952. For example, the outer surface of the tubes 952 may be molded or formed to have ridges, braids, or some other type of texture. In another aspect, an additional bioabsorbable or biocompatible treatment may be applied to the outer surface of the tubes 952 to create the rough surface. Any and all aspects, and any variation thereof, are contemplated as being within aspects herein.

Figure 10A:
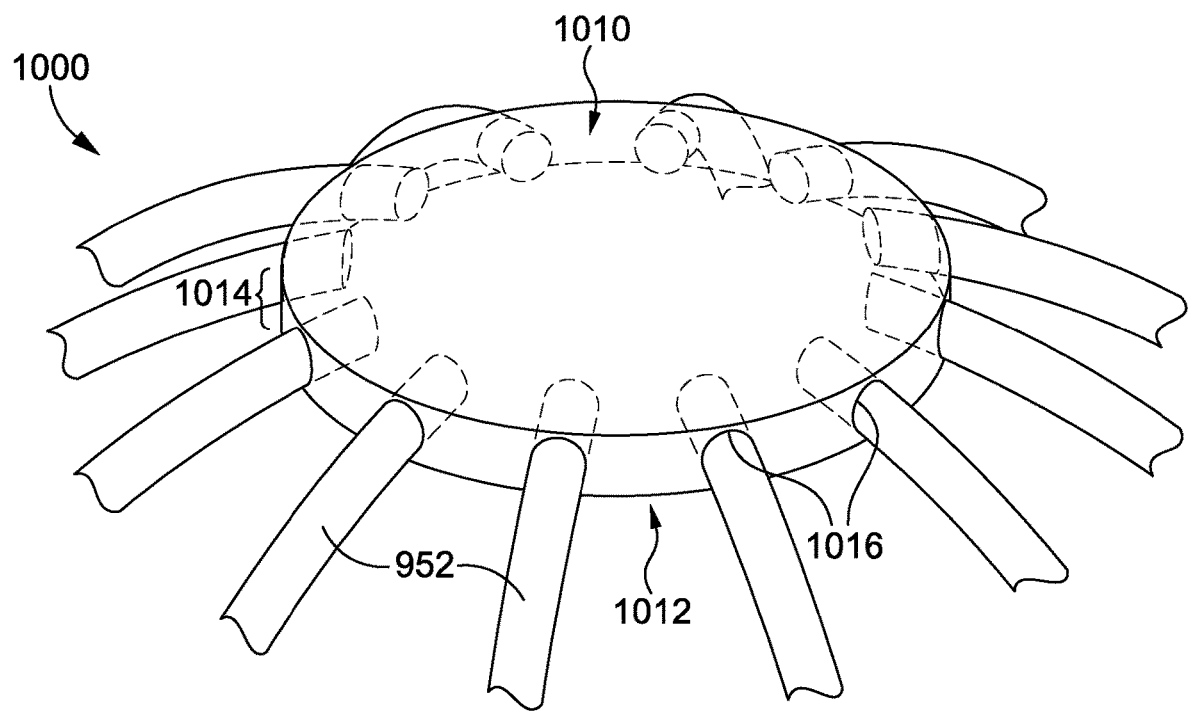
FIG. 10A illustrates a close-up view of a first exemplary configuration for the hub of the fifth exemplary brachytherapy device of FIG. 9C.
Figure 10B:
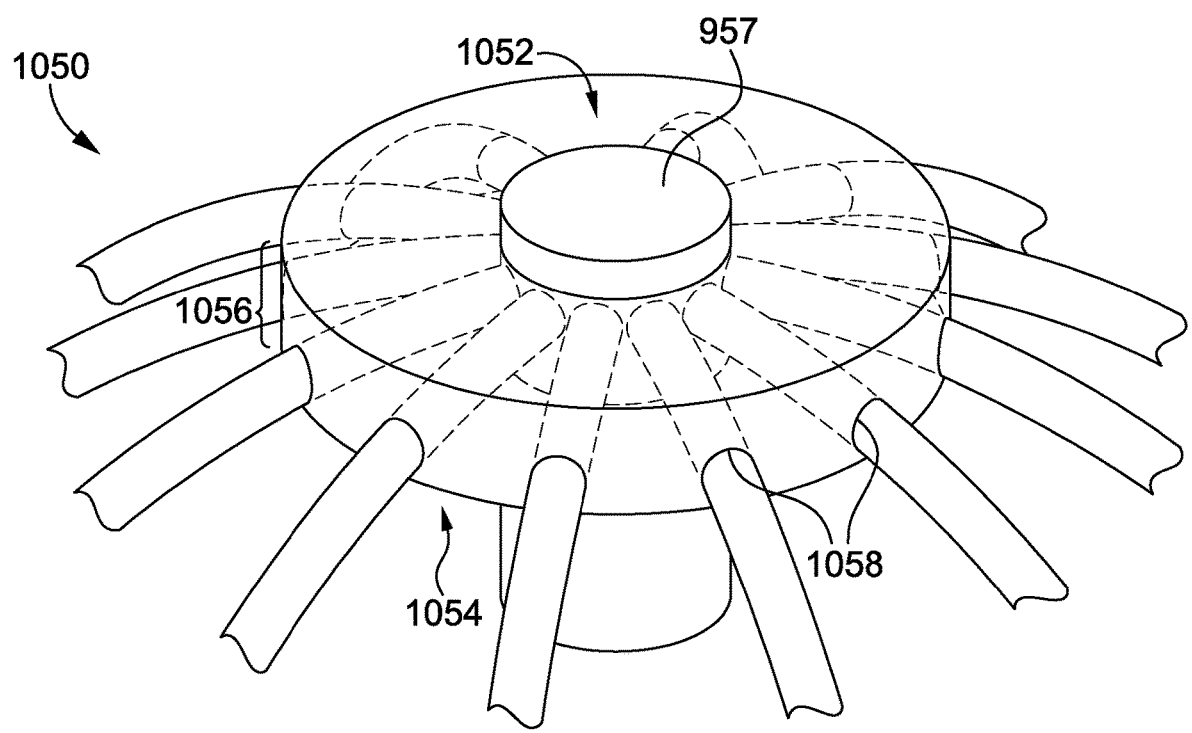
FIG. 10B illustrates a close-up view of a second exemplary configuration for the hub of the fifth exemplary brachytherapy device of FIG. 9C.

With respect to the first planar hub 958 and the second planar hub 960, aspects herein contemplate a number of different configurations for the hubs 958 and 960 as shown by FIGS. 10A and 10B. FIG. 10A depicts an exemplary hub 1000 having a first surface 1010, a second surface 1012 opposite the first surface 1010, and a side wall 1014 extending therebetween. The exemplary hub 1000 may comprise the first planar hub 958 and/or the second planar hub 960. The side wall 1014 of the hub 1000 further comprises a plurality of receiving holes 1016 evenly spaced around the circumference of the hub 1000. Each receiving hole 1016 extends a predetermined distance towards the center of the hub 1000 (shown by the dashed lines). Exemplary distances may comprise, for example, from about 2 mm to about 10 mm, from about 2 mm to about 8 mm, or from about 2 mm to about 5 mm. In general, the number of receiving holes 1016 is equal to the number hollow tubes 952 forming the brachytherapy device 950 (excluding the central column).

In use, the tubes 952 may be loaded with radioactive seeds or strands, radiopaque markers, and/or active elements and the tube ends may be fed into the receiving holes 1016 and secured using, for instance, a medical adhesive. This step may occur at, for instance, the manufacturing facility making the brachytherapy device 950 or may occur at the time of intra-operative placement.

FIG. 10B depicts an alternative configuration for the planar hubs 958 and/or 960 in accordance with aspects herein. FIG. 10B depicts a hub 1050 having a first surface 1052, a second surface 1054 opposite the first surface 1052, and a side wall 1056 extending therebetween. The side wall 1056 of the hub 1050 further comprises a plurality of receiving holes 1058 evenly spaced around the circumference of the hub 1050. Each receiving hole 1058 extends to the center of the hub 1050 (shown by the dashed lines). To describe this differently, each hole 1058 extends to the central column 957. In general, the number of receiving holes 1058 is equal to the number hollow tubes 952 forming the brachytherapy device 950 (excluding the central column).

Similar to the planar hub 1000, in use the tubes 952 may be loaded with radioactive seeds or strands, radiopaque markers, and/or active elements and the tube ends may be fed into the receiving holes 1058 and secured using, for instance, a medical adhesive. This step may occur at, for instance, the manufacturing facility making the brachytherapy device 950 or may occur at the time of intra-operative placement.

Aspect 5

Figure 11:
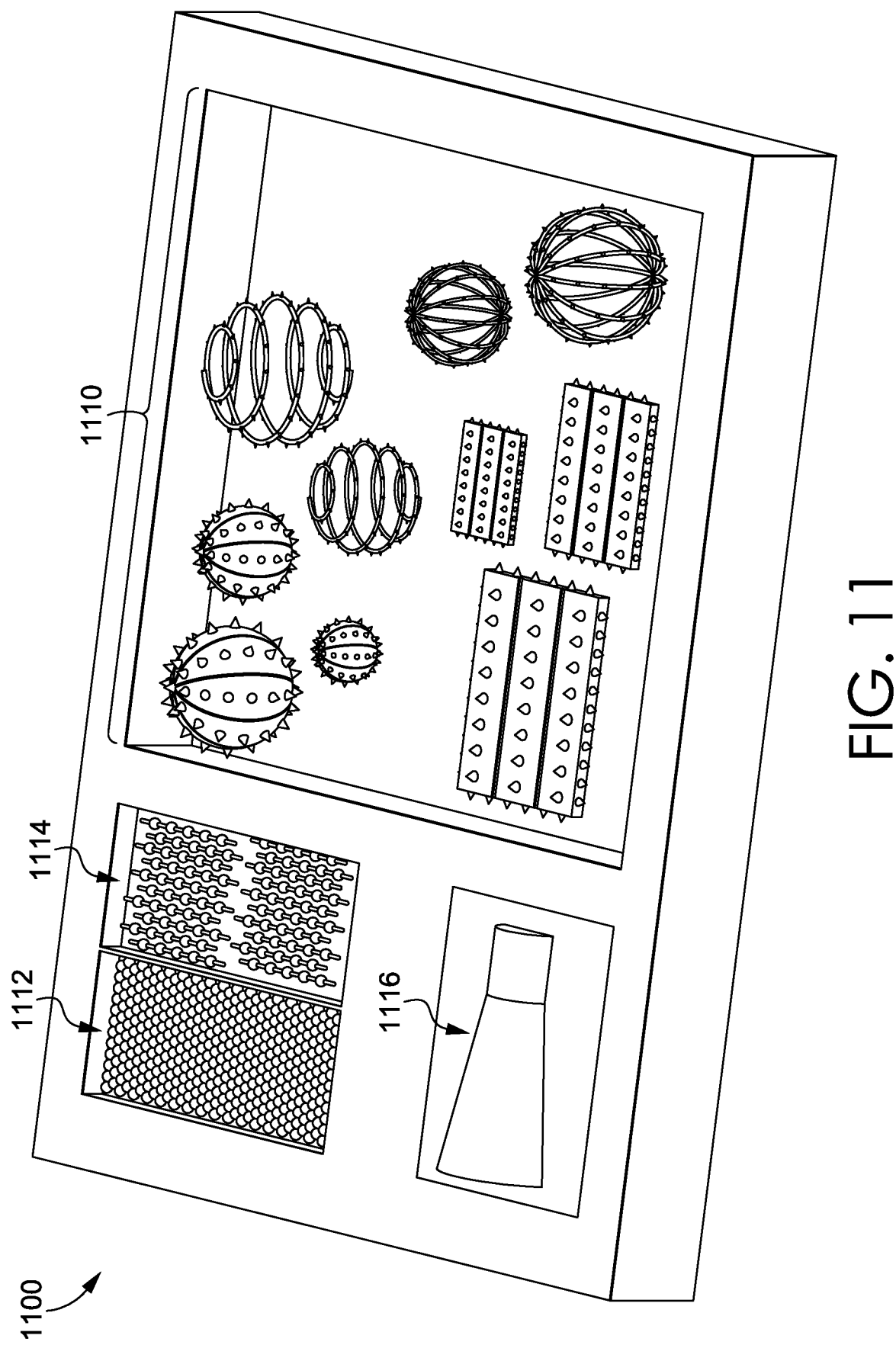
FIG. 11 illustrates an exemplary kit comprising at least radioactive seeds/strands and/or radiopaque markers and one or more brachytherapy devices in a number of predetermined sizes in accordance with aspects herein.

Turning now to FIG. 11, aspects herein further contemplate a brachytherapy kit 1100. In exemplary aspects, the kit 1100 includes a plurality of brachytherapy devices 1110 such as the device 100, the device 200, the device 300, the devices 600 and 650, and/or the devices 900, 925, and 950 in a number of predetermined sizes as described above. The kit 1100 further includes loose radioactive seeds (high dose and low dose) 1112, radioactive strands (high dose and low dose) 1114, radiopaque markers (not shown), and/or other types of active elements (not shown). The kit 1100 may optionally include a medical adhesive 1116, computer software useable for determining an appropriate radiation dose and/or an appropriate device configuration to use (not shown), and/or Babcok forceps with long arms for placement of the loaded brachytherapy device in the tumor bed (not shown). The brachytherapy kit 1100 would come in a sterile form and is meant to be used in the operating room during the resection of a tumor.

In a use scenario, a surgeon and a radiation oncologist would be present in the operating room. After the tumor is removed and a preliminary reading is received from the pathologist, the radiation oncologist would determine the appropriate type, shape and size of the brachytherapy device depending on the size and shape configuration of the tumor bed and where the tumor bed is located. For instance, when the tumor is located in the brain, the radiation oncologist may select the brachytherapy device 600, 650, 900, 925, or 950 since these are non-space occupying (or minimally-space occupying) devices, and these devices would generally not increase pressure in the organ in which they are placed (an important consideration in the brain). In another example, when the tumor is located in the breast, the radiation oncologist may select the brachytherapy device 100 or 200. By using a solid, space-occupying device with this type of tumor, the device may help to fill the tumor bed and produce a better visual aesthetic to the breast after lumpectomy. In yet another example, when the tumor is a sarcoma or other similar types of tumor, the radiation oncologist may select the brachytherapy device 300. By using a 2-D shape with grooves and seeds located on just one planar surface, the device can be positioned such that the radioactive seeds are next to the tumor bed and not adjacent to healthy tissue.

Continuing, the radiation oncologist would also determine an appropriate radiation dose depending on the grade of the tumor. Based on this, the radiation oncologist would load the selected brachytherapy dose with the appropriate dose of radiation using the seeds 1112 and/or strands 1114 in the kit 1100. The loaded brachytherapy device would then be positioned within the tumor bed by the surgeon, and the surgeon would proceed with closing the surgical wound.

It is also contemplated herein that the kit 1100 may come with a variety of pre-loaded brachytherapy devices in one or more sizes and shape configurations. In other words, the radioactive seeds/strands/markers/elements would be positioned in or on the brachytherapy device at the time of manufacture and the pre-loaded devices would then be shipped. It is also contemplated herein, that brachytherapy kits may be customized based on tumor type. For instance, there may be a breast brachytherapy kit having devices such as device 100 and/or device 200 in a number of predetermined sizes. There may be a brain brachytherapy kit having devices 600, 650, 900, 925, and/or 950 in a number of predetermined sizes. As well, there may be a sarcoma brachytherapy kit having device 300 in a number of predetermined sizes. These are just illustrative examples, and it is contemplated that brachytherapy kits may be customized for any number and type of tumors.

Aspect 6

Figure 12:
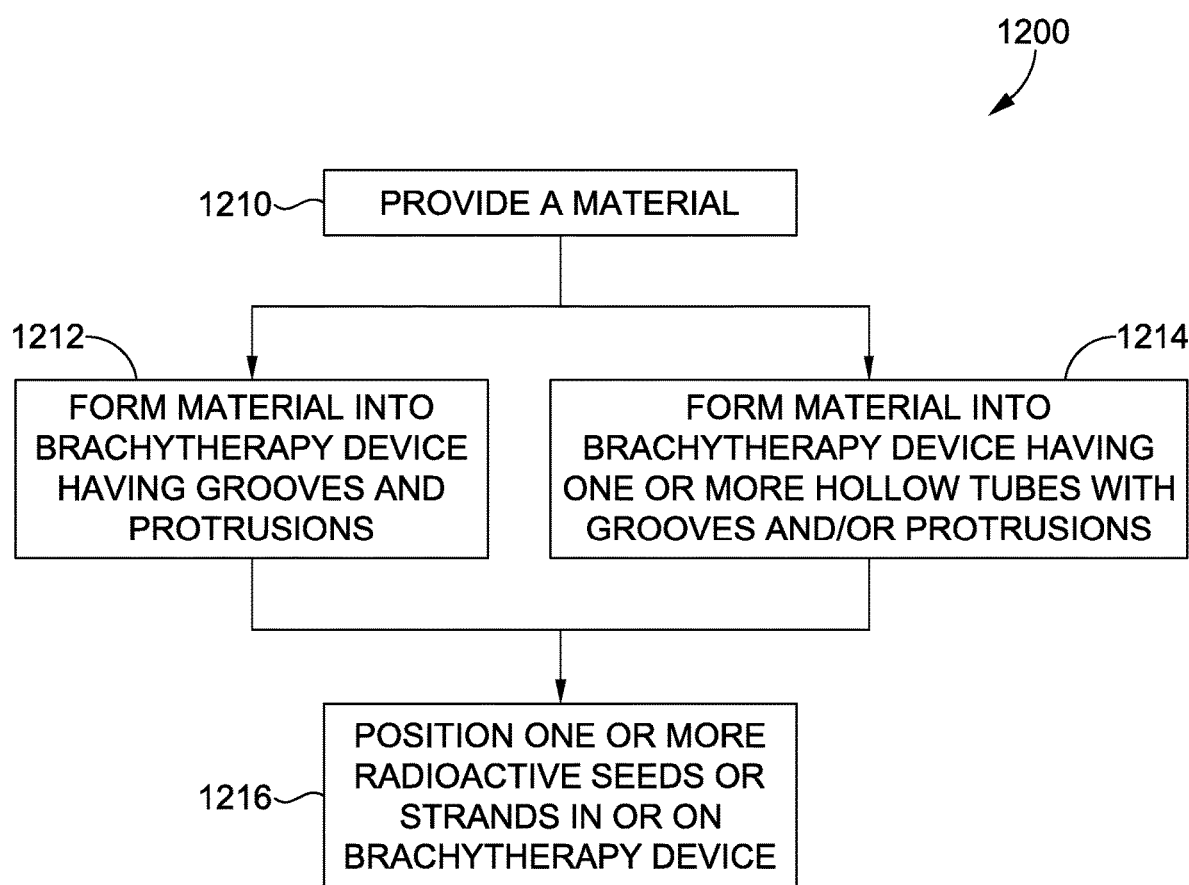
FIG. 12 illustrates a flow diagram of an exemplary method of forming a brachytherapy device in accordance with aspects herein.

Aspects herein further contemplate a method of manufacturing a brachytherapy device as shown in FIG. 12. FIG. 12 depicts a flow diagram of an exemplary method 1200 of manufacturing a brachytherapy device, such as any of the brachytherapy devices 100, 200, 500, 600, 650, 900, 925, or 950 in accordance with aspects herein. At a step 1210, a material is provided. The material may comprise a silicone (polysiloxane) polymer, silastic (polydimethylsiloxane), PEEK, polyglycolic acid, L or D polylactic acid, or any combination thereof.

Continuing, in one exemplary aspect and as indicated at a step 1212, the material is formed into a brachytherapy device having grooves, protrusions, and optional central channels such as illustrated for the brachytherapy devices 100, 200, and 500. In another exemplary aspect, and as indicated at a step 1214, the material is formed into a brachytherapy device having one or more hollow tubes with grooves or protrusions on the outer surface of the tubes such as illustrated for the brachytherapy devices 600, 650, 900, 925, and 950. The material may be formed into a brachytherapy device using complementary molds, injection molding, 3-D printing, and the like. The steps 1212 and 1214 may further comprise an optional curing step. In one exemplary aspect, the steps 1210, 1212 or 1214 may take place at a manufacturing facility. When done at a manufacturing facility, the brachytherapy device may be formed into one of the device configurations shown for the devices 100, 200, 500, 600, 650, 900, 925, and 950 and may be further formed into one of a predetermined number of sizes as described above.

Continuing, in another exemplary aspect, the steps 1210, 1212 or 1214 may take place in an operating room setting at the time a tumor is being removed. This may be particularly useful for when the tumor bed has an irregular shape that does not correspond to the shapes/configurations associated with the devices 100, 200, 500, 600, 650, 900, 925, and 950. Exemplary tumors that may fall within this category include, for example, sacral convexity tumors, paraspinal tumors, and irregular shaped brain tumors. To provide effective radiation delivery for these types of tumors, a brachytherapy device having a customized shape may be useful. In exemplary aspects, the tumor bed may be scanned using for example, known laser scanning techniques, and the information inputted into a 3-D printer. The 3-D printer would be utilized to form a brachytherapy device having a shape corresponding to the shape of the tumor bed and having one or more of the features describes for the brachytherapy devices 100, 200, 500, 600, 650, 900, 925, or 950.

The method 1200 may further comprise, at a step 1216, positioning one or more radioactive seeds, strands, radiopaque markers, and/or active elements within one or more grooves of the brachytherapy device or within one or more channels when the brachytherapy device is formed using hollow tubes. In one exemplary aspect, the formed and loaded brachytherapy device may be packaged separately or as part of a kit and shipped to its destination end point. In an alternative step, the formed brachytherapy device may not be pre-loaded and, instead, may be packaged separately or as part of a kit and shipped to its destination end point. With respect to this aspect, the brachytherapy device may be loaded with radioactive seeds/strands or radiopaque markers at the time of intra-operative placement. Any and all aspects, and any variation thereof, are contemplated as being within aspects herein.

Aspects of the present disclosure have been described with the intent to be illustrative rather than restrictive. Alternative aspects will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

What is claimed is:

1. A method of using a brachytherapy device comprising:
    positioning the brachytherapy device within a tumor bed, wherein the brachytherapy device comprises a plurality of tubes arranged in a spherical or ellipsoid form, each tube of the plurality of tubes having a respective first end and a respective second end, wherein the first ends of the plurality of tubes are joined at a first pole of the spherical or ellipsoid form, and wherein the second ends of the plurality of tubes are joined at a second opposite pole of the spherical or ellipsoid form, the each tube having a tube channel extending along at least a portion of a length of the each tube, the brachytherapy device further comprising one or more active elements positioned within one or more of the tube channels; and
    completely enclosing the brachytherapy device within the tumor bed.

2. The method of using the brachytherapy device of claim 1, wherein the brachytherapy device is positioned within the tumor bed at a time of removal of a tumor located within the tumor bed.

3. A brachytherapy kit comprising:
    a plurality of brachytherapy devices configured to be completely enclosed within a tumor bed, at least one brachytherapy device of the plurality of brachytherapy devices comprising a plurality of tubes arranged in a spherical or ellipsoid form having a fixed diameter, each tube of the plurality of tubes having a respective first end and a respective second end, wherein the first ends of the plurality of tubes are joined at a first pole of the spherical or ellipsoid form, and wherein the second ends of the plurality of tubes are joined at a second opposite pole of the spherical or ellipsoid form, the each tube having a tube channel extending along at least a portion of a length of the each tube; and
    one or more active elements.

4. The brachytherapy kit of claim 3, wherein the one or more active elements include one or more loose radioactive seeds and radioactive strands.

5. The brachytherapy kit of claim 3, further comprising a medical adhesive.

6. The brachytherapy kit of claim 3, further comprising forceps.

7. The brachytherapy kit of claim 3, wherein the brachytherapy kit is packaged in a sterile form.

8. The brachytherapy kit of claim 3, wherein the fixed diameter of the at least one brachytherapy device is from about 2 cm to about 7 cm.

9. The brachytherapy kit of claim 3, wherein the one or more active elements are pre-loaded within at least a portion of the plurality of brachytherapy devices.

10. A brachytherapy device comprising:
    a plurality of tubes arranged in a form having a fixed diameter, each tube of the plurality of tubes having a respective first end and a respective second end, wherein the first ends of the plurality of tubes are joined at a first pole of the form, and wherein the second ends of the plurality of tubes are joined at a second opposite end of the form, the each tube having a tube channel that extends along at least a portion of a length of each tube; and
    one or more active elements positioned within one or more of the tube channels, wherein the brachytherapy device is configured to be completely enclosed within a tumor bed.

11. The brachytherapy device of claim 10, wherein the tube channel extends from the first end to the second end of the each tube.

12. The brachytherapy device of claim 10, wherein the one or more active elements have one or more of pharmaceutical, nuclear, and radioactive properties.

* * * * *